(12) United States Patent
Paulsen et al.

(10) Patent No.: US 10,993,298 B2
(45) Date of Patent: *Apr. 27, 2021

(54) LIGHTING DEVICES AND METHODS FOR USE

(71) Applicants: Gary Paulsen, Chicago, IL (US); David Basken, Chicago, IL (US); Matthew Muller, Chicago, IL (US)

(72) Inventors: Gary Paulsen, Chicago, IL (US); David Basken, Chicago, IL (US); Matthew Muller, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/708,563

(22) Filed: Dec. 10, 2019

(65) Prior Publication Data

US 2020/0113028 A1 Apr. 9, 2020

Related U.S. Application Data

(63) Continuation of application No. 16/545,853, filed on Aug. 20, 2019, now Pat. No. 10,631,385, which is a
(Continued)

(51) Int. Cl.
| | |
|---|---|
| *H05B 45/20* | (2020.01) |
| *A61M 21/02* | (2006.01) |
| *A61M 21/00* | (2006.01) |

(52) U.S. Cl.
CPC .............. *H05B 45/20* (2020.01); *A61M 21/02* (2013.01); *A61M 2021/0044* (2013.01); *A61M 2205/587* (2013.01)

(58) Field of Classification Search
CPC .............. H05B 33/0857; A61M 21/02; A61M 2021/0044; A61M 2205/587
See application file for complete search history.

(56) References Cited

U.S. PATENT DOCUMENTS 9,913,341 B2 * 3/2018 Maxik .................... F21K 9/232
2015/0062892 A1 3/2015 Krames et al.
(Continued)

FOREIGN PATENT DOCUMENTS

DE 10 2014 115 079 A1 4/2016

OTHER PUBLICATIONS

International Search Report and Written Opinion of the International Searching Authority dated Aug. 6, 2018, issued in connection with International Application No. PCT/US2018/020395, filed on Mar. 1, 2018, 19 pages.
(Continued)

*Primary Examiner* — Daniel D Chang
(74) *Attorney, Agent, or Firm* — McDonnell Boehnen Hulbert & Berghoff LLP

(57) ABSTRACT

An example device is configured to emit a first light having a first luminous flux and a peak intensity at a first wavelength that is greater than or equal to 400 nanometers (nm) and less than or equal to 480 nm. The first luminous flux is variable and/or the emission of the first light is interrupted one or more times. The device is also configured to emit a second light having a second luminous flux and a peak intensity at a second wavelength that is greater than or equal to 500 nm and less than or equal to 630 nm. The second luminous flux is variable and/or the emission of the second light is interrupted one or more times. The first luminous flux is at a maximum at least during a time at which the second luminous flux is not at a maximum.

20 Claims, 13 Drawing Sheets

Related U.S. Application Data continuation of application No. 15/943,210, filed on Apr. 2, 2018, now Pat. No. 10,433,389, which is a continuation of application No. PCT/US2018/020395, filed on Mar. 1, 2018.

(60) Provisional application No. 62/546,475, filed on Aug. 16, 2017, provisional application No. 62/508,286, filed on May 18, 2017.

(56) References Cited

U.S. PATENT DOCUMENTS

| | | | |
|---|---|---|---|
| 2015/0123564 A1* | 5/2015 | Simonian | H05B 37/0227 315/294 |
| 2016/0023017 A1 | 1/2016 | Moore-Ede et al. | |
| 2016/0193478 A1 | 7/2016 | Maxik et al. | |
| 2017/0080249 A1 | 3/2017 | Brawn et al. | |

OTHER PUBLICATIONS

Figueiro et al., "Preliminary evidence that light through the eyelids can suppress melatonin and phase shift dim light melatonin onset," BMC Research Notes, vol. 5, No. 221, May 7, 2012, pp. 1-9.
Mien et al., "Effects of Exposure to Intermittent versus Continuous Red Light on Human Circadian Rhythms, Melatonin Suppression, and Pulillary Constriction," PLOS One, vol. 9, No. 5, E96532, May 5, 2014, pp. 1-8.

* cited by examiner

LIGHTING DEVICES AND METHODS FOR USE

CROSS-REFERENCE TO RELATED APPLICATIONS

This application is a continuation of U.S. patent application Ser. No. 16/545,853, filed on Aug. 20, 2019, which is a continuation of U.S. patent application Ser. No. 15/943,210, filed on Apr. 2, 2018, which claims the benefit of U.S. Provisional Patent Application No. 62/508,286, filed on May 18, 2017, claims the benefit of U.S. Provisional Patent Application No. 62/546,475, filed on Aug. 16, 2017, and claims the benefit of International (PCT) Application No. PCT/US2018/020395, filed on Mar. 1, 2018, the contents of all of which are incorporated herein by reference in their entirety.

BACKGROUND

Unless otherwise indicated herein, the materials described in this section are not prior art to the claims in this application and are not admitted to be prior art by inclusion in this section.

It may be useful to alter a person's circadian rhythm or "sleep cycle" for reasons such as jet lag and adjustment to non-traditional work shifts. A person's circadian rhythm is principally governed by the suprachiasmatic nucleus (SCN), which is a small region within the brain's hypothalamus. Previous methods for altering a person's circadian rhythm have generally involved direct stimulation of the light-sensitive protein melanopsin within intrinsically photosensitive retinal ganglion cells (ipRGCs) that make up about 1% of retinal ganglion cells within the retina. It is thought that illumination of the retina with blue light (e.g, peak wavelength of about 480 nanometers) causes melanopsin excited within a person's ipRGCs to stimulate the SCN via neural pathways, thereby altering the person's circadian rhythm (e.g., delaying the onset of tiredness). However, due to the ipRGCs' relatively low photosensitivity, their relatively sparse presence within the retina, and slow photoactive response, such methods may undesirably involve illuminating the retina with intensities that are unpleasant or even painful, for relatively long periods of time.

SUMMARY

One example describes a device that includes a light source assembly and a control system configured to cause the light source assembly to perform functions. The functions include emitting a first light having a first luminous flux and a peak intensity at a first wavelength that is greater than or equal to 400 nanometers (nm) and less than or equal to 480 nm. The first luminous flux is variable or the emission of the first light is interrupted one or more times. The functions further include emitting a second light having a second luminous flux and a peak intensity at a second wavelength that is greater than or equal to 500 nm and less than or equal to 630 nm. The second luminous flux is variable or the emission of the second light is interrupted one or more times. The first luminous flux is at a maximum at least during a time at which the second luminous flux is not at a maximum.

Another example describes a method that includes emitting, via a light source assembly, a first light having a first luminous flux and a peak intensity at a first wavelength that is greater than or equal to 400 nanometers (nm) and less than or equal to 480 nm. The first luminous flux is variable or the emission of the first light is interrupted one or more times. The method further includes emitting, via the light source assembly, a second light having a second luminous flux and a peak intensity at a second wavelength that is greater than or equal to 500 nm and less than or equal to 630 nm. The second luminous flux is variable or the emission of the second light is interrupted one or more times. The first luminous flux is at a maximum at least during a time at which the second luminous flux is not at a maximum.

Yet another example describes a white light source having a color rendering index of greater than 70 as compared to daylight, a blackbody, or another lighting reference standard. The white light source is configured to emit light with a peak wavelength within a range of 480 nm to 580 nm.

Yet another example describes a light source that includes one or more discrete light emitting diodes (LEDs) configured to emit first light having a peak intensity within a range of 480 nm to 560 nm. The light source further includes one or more white LEDs having a color rendering index higher than 70 when compared to daylight, a blackbody, or another lighting reference standard, the one or more white LEDs being configured to emit second light such that the first light and the second light combined have a peak intensity at a wavelength within a range of 480 nm to 580 nm.

Yet another example describes a device that includes a light source assembly and a control system configured to cause the light source assembly to emit light having a luminous flux and a peak intensity at a wavelength that is greater than or equal to 400 nanometers (nm) and less than or equal to 480 nm. The luminous flux is variable or the emission of the light is interrupted one or more times.

Yet another example describes one or more light sources configured to emit: a first light having a peak wavelength within a range of 470 nm to 580 nm and a second white light having a color rendering index of greater than 70 when compared to daylight, a blackbody, or another lighting reference standard. A luminous flux of the second light is less than a luminous flux of the first light.

Yet another example describes one or more light sources configured to emit: a first light having a peak wavelength within a range of 600 nm to 700 nm and a second white light having a color rendering index of greater than 70 when compared to daylight, a blackbody, or another lighting reference standard. A luminous flux of the second light is less than a luminous flux of the first light.

Yet another example describes a device that includes one or more light sources configured to emit first light having a color rendering index of greater than 70 when compared to daylight, a blackbody, or another lighting reference standard, and one or more phosphors that, when illuminated by the one or more light sources, emit second light such that the first light and the second light combined have a peak intensity at a wavelength within a range of 470 nm to 580 nm.

Yet another example describes a device that includes a light source assembly and a control system configured to cause the light source assembly to perform functions. The functions include emitting a first light having a first luminous flux and a peak intensity at a first wavelength that is greater than or equal to 400 nanometers (nm) and less than or equal to 440 nm. The first luminous flux is variable or the emission of the first light is interrupted one or more times. The functions further include emitting a second light having a second luminous flux and having a color correlated temperature of greater than or equal to 2500 Kelvin and less than or equal to 6000 Kelvin. The second luminous flux is variable or the emission of the second light is interrupted one or more times and the second light has a color rendering index greater than 70 when compared to daylight, a blackbody, or another lighting reference standard. The first luminous flux is at a maximum at least during a time at which the second luminous flux is not at a maximum.

Yet another example describes a method that includes emitting, via a light source assembly, a first light having a first luminous flux and a peak intensity at a first wavelength that is greater than or equal to 400 nanometers (nm) and less than or equal to 440 nm. The first luminous flux is variable or the emission of the first light is interrupted one or more times. The method further includes emitting, via the light source assembly, a second light having a second luminous flux and having a color correlated temperature of greater than or equal to 2500 Kelvin and less than or equal to 6000 Kelvin. The second luminous flux is variable or the emission of the second light is interrupted one or more times. The second light has a color rendering index greater than 70 when compared to daylight, a blackbody, or another lighting reference standard. The first luminous flux is at a maximum at least during a time at which the second luminous flux is not at a maximum.

Yet another example describes a plurality of light sources configured to emit light having a peak wavelength within a range of 400 nm to 440 nm.

Yet another example describes a white light source having a color rendering index of greater than 70 as compared to daylight, a blackbody, or another lighting reference standard. The white light source is configured to emit light with a peak wavelength within a range of 400 nm to 440 nm.

Yet another example describes a device that includes a light source assembly; and a control system configured to cause the light source assembly to perform functions comprising: emitting a first light having a first luminous flux and a peak intensity at a first wavelength that is greater than or equal to 680 nanometers (nm) and less than or equal to 750 nm, wherein the first luminous flux is variable or the emission of the first light is interrupted one or more times; and emitting a second light having a second luminous flux and a peak intensity at a second wavelength that is less than or equal to 680 nm, wherein the second luminous flux is variable or the emission of the second light is interrupted one or more times, wherein the first luminous flux is at a maximum at least during a time at which the second luminous flux is not at a maximum.

Yet another example describes a method that includes emitting, via a light source assembly, a first light having a first luminous flux and a peak intensity at a first wavelength that is greater than or equal to 680 nanometers (nm) and less than or equal to 750 nm, wherein the first luminous flux is variable or the emission of the first light is interrupted one or more times; and emitting, via the light source assembly, a second light having a second luminous flux and a peak intensity at a second wavelength that is less than or equal to 680 nm, wherein the second luminous flux is variable or the emission of the second light is interrupted one or more times, wherein the first luminous flux is at a maximum at least during a time at which the second luminous flux is not at a maximum.

Yet another example describes a device that includes a light source assembly; and a control system configured to cause the light source assembly to perform functions comprising: emitting a first light having a first luminous flux and a peak intensity at a first wavelength that is greater than or equal to 400 nanometers (nm) and less than or equal to 440 nm, wherein the first luminous flux is variable or the emission of the first light is interrupted one or more times; and emitting a second light having a second luminous flux and a peak intensity at a second wavelength that is greater than or equal to 440 nm, wherein the second luminous flux is variable or the emission of the second light is interrupted one or more times, wherein the first luminous flux is at a maximum at least during a time at which the second luminous flux is not at a maximum.

Yet another example describes a method that includes emitting, via a light source assembly, a first light having a first luminous flux and a peak intensity at a first wavelength that is greater than or equal to 400 nanometers (nm) and less than or equal to 440 nm, wherein the first luminous flux is variable or the emission of the first light is interrupted one or more times; and emitting, via the light source assembly, a second light having a second luminous flux and a peak intensity at a second wavelength that is greater than or equal to 440 nm, wherein the second luminous flux is variable or the emission of the second light is interrupted one or more times, wherein the first luminous flux is at a maximum at least during a time at which the second luminous flux is not at a maximum.

Yet another example includes a light source that includes one or more first light emitting diodes (LEDs) configured to emit first light having a peak intensity within a range of 400 nm to 440 nm; and one or more second LEDs configured to emit second light having a peak intensity greater than 440 nm, the first light and the second light combined having a peak intensity at a wavelength within a range of 400 nm to 440 nm.

Yet another example describes a method comprising: emitting, via one or more first light emitting diodes (LEDs) of a light source, first light having a peak intensity within a range of 400 nm to 440 nm; and emitting, via one or more second LEDs of the light source, second light having a peak intensity greater than 440 nm, the first light and the second light combined having a peak intensity at a wavelength within a range of 400 nm to 440 nm.

These, as well as other aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrate the invention by way of example only and, as such, that numerous variations are possible.

DETAILED DESCRIPTION

As discussed above, current methods for altering circadian rhythm via direct stimulation of melanopsin within intrinsically photosensitive retinal ganglion cells (ipRGCs) are often inconvenient, unpleasant, and/or somewhat ineffective. Accordingly, improved devices and methods for altering circadian rhythm are disclosed herein.

The present inventors have appreciated that circadian rhythm can be altered more conveniently and efficiently via stimulation of S-cones, M-cones, and L-cones within the eye, which causes indirect stimulation of ipRGCs that are downstream of the cones along neural pathways. Whereas previous methods involve illuminating ipRGCs with blue light (e.g., λ~480 nm) to optimize melanopsin photoactivity, the methods disclosed herein generally involve illuminating a retina with wavelengths optimized to stimulate S-cones having a maximum photosensitivity at about 420-440 nm, M-cones having a maximum photosensitivity at about 534-545 nm, and/or L-cones having a maximum photosensitivity at about 564-580 nm.

More specifically, the inventors have appreciated that stimulation of cones, which have a dense presence within the retina and higher photosensitivity when compared to ipRGCs, can cause more intense excitation of ipRGCs than direct stimulation of the ipRGCs themselves. This increased excitation of the ipRGCs causes increased stimulation of the suprachiasmatic nucleus (SCN), causing larger changes in circadian rhythm.

In particular, the inventors have appreciated that ipRGCs are most responsive to sharp increases and decreases in illuminance of the cones. For example, the activity of ipRGCs (and the resultant activity of the downstream SCN) is maximized in response to sharp increases in photoabsorption by M-cones (e.g., green light) and L-cones (e.g., red light), and sharp decreases in photoabsorption by S-cones (e.g., violet light).

Figure 1:
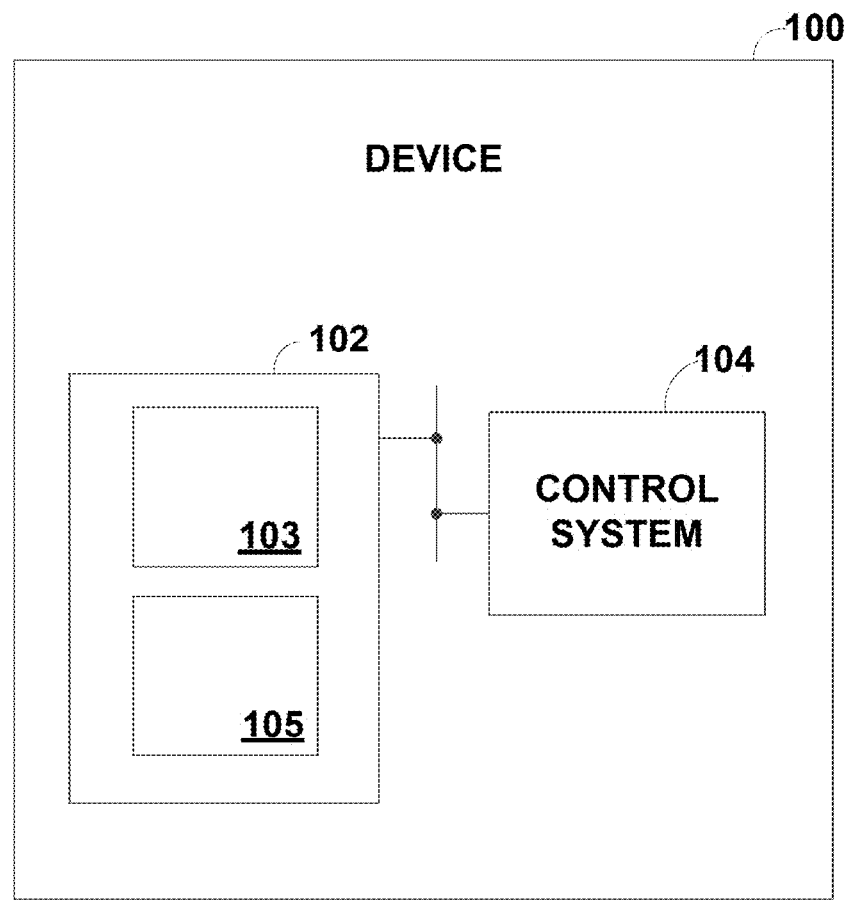
FIG. 1 is a schematic diagram of a lighting device, according to an example embodiment.

FIG. 1 depicts a (lighting) device 100 that includes a light source assembly 102 and a control system 104. In some examples, the light source assembly 102 may include one or more light sources such as light emitting diodes (LEDs), incandescent bulbs, or halogen bulbs, but other examples are possible.

The control system 104 may take the form of any combination of software and/or hardware that is configured to cause the light source assembly 102 and/or the device 100 to perform any of the functions that are described herein. For example, the control system 104 may include one or more Boolean circuits, programmable logic controllers (PLCs), and/or special purpose circuits configured to provide electrical power and/or control signals to the light source assembly 102 for performing any of the functions described herein. Additionally, the control system 104 may include one or more processors and a computer readable medium storing instructions that, when executed by the processors, cause the light source assembly 102 and/or the device 100 to perform any of the functions described herein. The control system 104 may additionally include a signal generator.

In various examples, the device 100 may be incorporated into or take the form of a wearable device, goggles, a headband, armwear, wristwear, or a therapeutic wearable device configured to shine light onto a subject's retina. In some examples, the device 100 is incorporated into a vehicle such as an automobile, an airplane, a helicopter, a boat, a ship, or a train. The device 100 could also be incorporated into a dashboard, an accent lighting unit, a cabin general lighting unit, or a headlight unit. In various examples, the device 100 is incorporated into a display unit such as a cell phone, a tablet computer, a monitor, or a television. The device 100 could also be incorporated into a lighting unit such as a lamp, a nightlight, a chandelier, or an overhead lighting unit.

In some embodiments, the device 100 may take the form of a white light source having a color rendering index of greater than 70 as compared to daylight, a blackbody, or another lighting reference standard, with the white light source being configured to emit light with a peak wavelength within a range of 480 nm to 580 nm, or more specifically, within a range of 520 nm to 570 nm.

In some embodiments, the device 100 takes the form of a light source that includes one or more discrete light emitting diodes (LEDs) configured to emit first light having a peak intensity within a range of 480 nm to 560 nm, and one or more white LEDs having a color rendering index higher than 70 when compared to daylight, a blackbody, or another lighting reference standard, the one or more white LEDs being configured to emit second light such that the first light and the second light combined have a peak intensity at a wavelength within a range of 480 nm to 580 nm. In this context, the device 100 could be operated in the presence of ambient light having one or more wavelengths within a range of 400 nm to 780 nm. In this context, at least 50%, at least 60%, at least 70%, at least 80%, at least 90% or at least 95% of a power spectral density of the first light might correspond to wavelengths within a range of 480 nm to 560 nm.

The term "white light" as used herein may refer to any polychromatic light having a color rendering index greater than 70 as defined by the International Commission on Illumination (CIE) $R_a$ scale. Such white light may include non-zero intensities throughout the visible spectrum of 400-700 nm. As such, a "white light source" may include any light source configured to generate white light as described above. The term "color rendering index" (CRI) as used herein may also be generally defined with reference to the CIE $R_a$ scale.

In some embodiments, the control system 104 is configured to cause the light source assembly 102 to emit light having a luminous flux and a peak intensity at a wavelength that is greater than or equal to 400 nanometers (nm) and less than or equal to 480 nm, the luminous flux being variable or the emission of the light being interrupted one or more times. More specifically, the peak intensity may occur within any of the following wavelength ranges: 410-430 nm, 415-425 nm, 418-422 nm (as measured by a spectrophotometer having a tolerance of +/−2 nm). Such luminous flux may take the form of a square wave, a sinusoidal wave, a sawtooth wave, or a triangle wave. The luminous flux may be periodic with a frequency that is less than or equal to 100 Hz, or less than or equal to 50 Hz. In this context, at least 50%, at least 60%, at least 70%, at least 80%, at least 90% or at least 95% of a power spectral density of the light might correspond to wavelengths within a range of 400 nm to 480 nm. Additionally, the luminous flux might periodically reach a minimum that is greater than zero or equal to zero.

The device 100 may be configured to illuminate a retina of a user with an illuminance that is less than or equal to 10,000 lux, less than or equal to 5,000 lux, less than or equal to 1,000 lux, less than or equal to 500 lux, less than or equal to 100 lux, less than or equal to 50 lux, less than or equal to 10 lux, or less than or equal to 1 lux. In this context, illuminance is defined as $Ev=\Phi V/(4\pi r2)$, with 'f' being the distance from the light source to the retina and $\Phi V$ being the luminous flux of the light source.

In another example, the device 100 may take the form of one or more light sources configured to emit: a first light having a peak wavelength within a range of 470 nm to 580 nm; and a second white light having a color rendering index of greater than 70 when compared to daylight, a blackbody, or another lighting reference standard, the luminous flux of the second light being less than a luminous flux of the first light. In this context, at least 50%, at least 60%, at least 70%, at least 80%, at least 90% or at least 95% of a power spectral density of the first light might correspond to wavelengths within a range of 470 nm to 580 nm.

In another example, the device 100 may take the form one or more light sources configured to emit: a first light having a peak wavelength within a range of 600 nm to 700 nm; and a second white light having a color rendering index of greater than 70 when compared to daylight, a blackbody, or another lighting reference standard, the luminous flux of the second light being less than a luminous flux of the first light. In this context, at least 50%, at least 60%, at least 70%, at least 80%, at least 90% or at least 95% of a power spectral density of the first light might correspond to wavelengths within a range of 600 nm to 700 nm.

In another example, the device 100 may take the form of one or more light sources configured to emit first light having a color rendering index of greater than 70 when compared to daylight, a blackbody, or another lighting reference standard; and one or more phosphors that, when illuminated by the one or more light sources, emit second light such that the first light and the second light combined have a peak intensity at a wavelength within a range of 470 nm to 580 nm. In this context, at least 50%, at least 60%, at least 70%, at least 80%, at least 90% or at least 95% of a power spectral density of the second light might correspond to wavelengths within a range of 470 nm to 580 nm.

Figure 2:
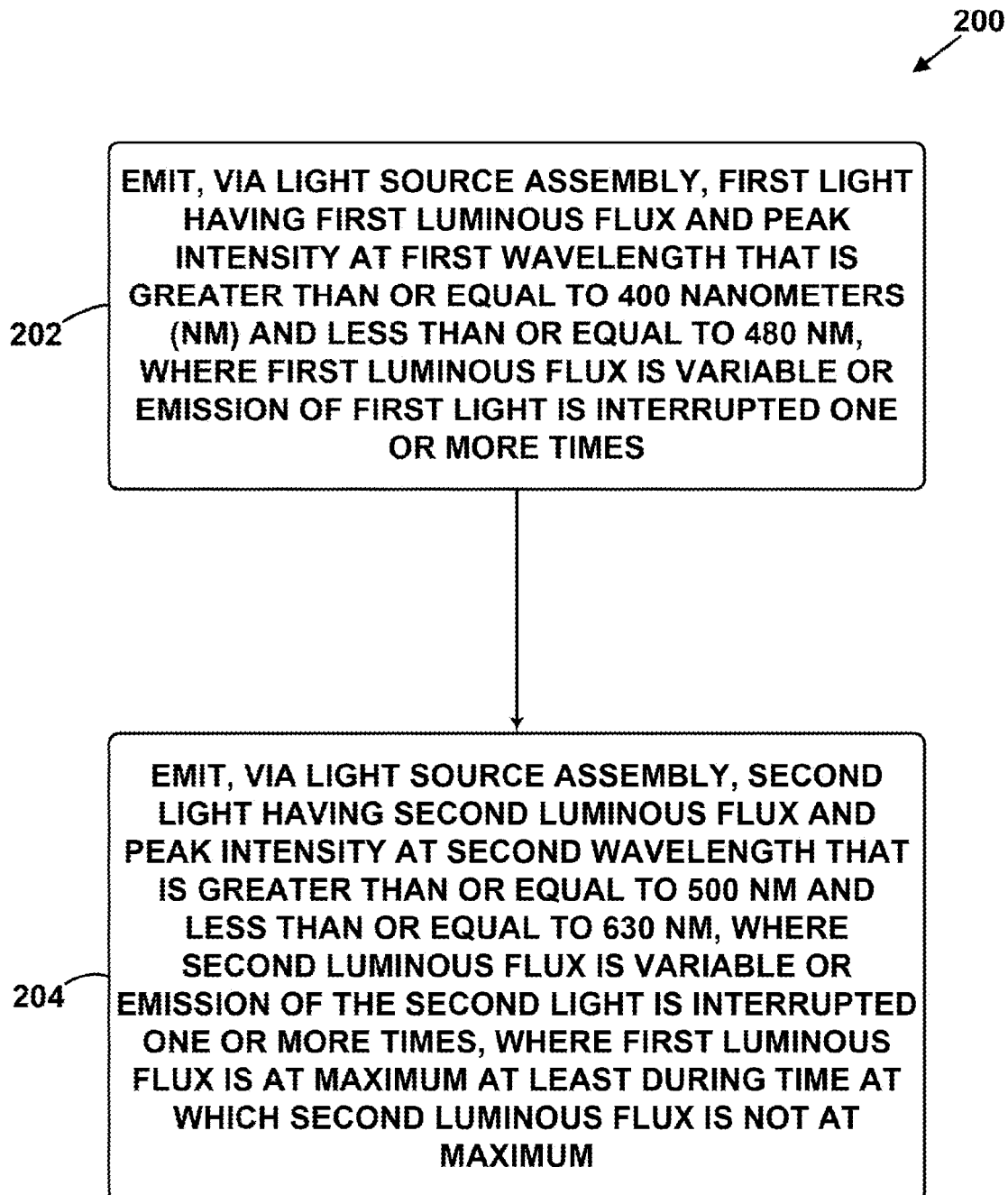
FIG. 2 is a block diagram of a method, according to an example embodiment.

FIG. 2 is a block diagram of a method 200. The method 200 and related methods disclosed herein can be performed to cause advancement or delay of a subject's circadian cycle for various purposes. Such methods can be performed to treat a subject afflicted with seasonal affective disorder (SAD) or another mood disorder, such as depression, bipolar disorder, or dysthymia. Disrupted or irregular sleep can also affect those suffering with cancer and/or heart disease, and these methods can be used accordingly to counteract such effects.

At block 202, the method includes emitting, via a light source assembly, a first light having a first luminous flux and a peak intensity at a first wavelength that is greater than or equal to 400 nanometers (nm) and less than or equal to 480 nm. In other words, the first light may be most intense (or have a local maximum) at a wavelength that is greater than or equal to 400 nm and less than or equal to 480 nm. More specifically, the first wavelength may be greater than or equal to 410 nm and less than or equal to 430 nm, greater than or equal to 415 nm and less than or equal to 425 nm, or greater than or equal to 418 nm and less than or equal to 422 nm.

As the term is used throughout this disclosure, light defined as having a "peak intensity" within a certain range of wavelengths is not meant to exclude the possibility that the light might have a global peak intensity outside of the recited range of wavelengths. That is, the term "peak intensity" can refer to a local peak intensity and, in addition or in the alternative, to a global peak intensity.

In this context, the first luminous flux is variable or the emission of the first light is interrupted one or more times. For example, the first luminous flux may take the form of a square wave, a sinusoidal wave, a sawtooth wave, a triangle wave, or any digital or analog wave. Other examples are possible.

The first light may be emitted by the light source assembly 102 such that the first light illuminates a retina of a user with an illuminance that is less than or equal to 10,000 lux, less than or equal to 5,000 lux, less than or equal to 1,000 lux, less than or equal to 500 lux, less than or equal to 100 lux, less than or equal to 50 lux, less than or equal to 10 lux, or less than or equal to 1 lux.

Figure 3:
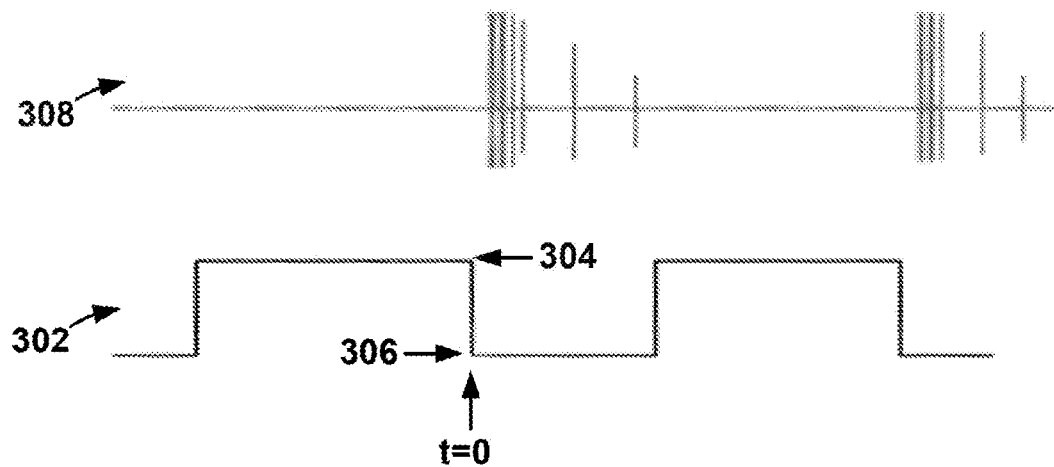
FIG. 3 illustrates intrinsically photosensitive retinal ganglion cell (ipRGC) response to excitation of S-type cones.

In one example, the light source assembly 102 emits a first light having a luminous flux 302 as shown in FIG. 3. The luminous flux 302 has a peak intensity at a wavelength that is greater than or equal to 400 nm and less than or equal to 480 nm. The luminous flux 302 takes the form of a square wave that oscillates between a high level of luminous flux 304 and a low level of luminous flux 306. The low level of luminous flux 306 could be zero or near zero, but the low level of luminous flux 306 is generally less than the high level of luminous flux 304. The luminous flux 302 having a peak intensity at a wavelength between 400-480 nm primarily excites S-cones within the retina, resulting in a response 308 of downstream ipRGCs. As shown, the response 308 is most frequent and intense immediately after the luminous flux 302 switches from the high level 304 to the low level 306 at t=0, for example. However, the response 308 continues at reduced intensity and frequency while the luminous flux 302 continues to be at the low level 306. The S-cones become relatively inactive after the luminous flux 302 switches to the high level 304.

In short, high response intensity and high response frequencies for downstream ipRGCs occur in response to relatively quick negative changes (decreases) in the luminous flux of the first light having a peak intensity between 400 and 480 nm. Although FIG. 3 shows the luminous flux 302 in the form of a square wave, waveforms such as a sinusoidal wave, a sawtooth wave, or a triangle wave can also exhibit relatively quick negative changes in luminous flux with peak intensity between 400 nm and 480, thereby efficiently exciting downstream ipRGCs.

In particular embodiments, at least 50%, at least 60%, at least 70%, at least 80%, at least 90% or at least 95% of a power spectral density of the first light corresponds to wavelengths within a range of 400 nm to 420 nm.

In particular embodiments, at least 50%, at least 60%, at least 70%, at least 80%, at least 90% or at least 95% of a power spectral density of the first light corresponds to wavelengths within a range of 420 nm to 440 nm.

In particular embodiments, at least 50%, at least 60%, at least 70%, at least 80%, at least 90% or at least 95% of a power spectral density of the first light corresponds to wavelengths within a range of 440 nm to 460 nm.

In particular embodiments, at least 50%, at least 60%, at least 70%, at least 80%, at least 90% or at least 95% of a power spectral density of the first light corresponds to wavelengths within a range of 460 nm to 480 nm.

In particular embodiments, the first luminous flux periodically reaches a minimum that is greater than zero.

In particular embodiments, the first luminous flux periodically reaches a minimum that is equal to zero. At block 204, the method includes emitting, via the light source assembly, a second light having a second luminous flux and a peak intensity at a second wavelength that is greater than or equal to 500 nm and less than or equal to 630 nm. In other words, the second light may be most intense (or have a local maximum) at a wavelength that is greater than or equal to 500 nm and less than or equal to 630 nm. More specifically, the second wavelength may be greater than or equal to 535 nm and less than or equal to 565 nm, greater than or equal to 545 nm and less than or equal to 555 nm, or greater than or equal to 548 nm and less than or equal to 552 nm.

In this context, the second luminous flux is variable or the emission of the second light is interrupted one or more times. For example, the second luminous flux may take the form of a square wave, a sinusoidal wave, a sawtooth wave, a triangle wave, or any other digital or analog wave. Other examples are possible.

The second light may be emitted by the light source assembly 102 such that the second light illuminates a retina of a user with an illuminance that is less than or equal to 10,000 lux, less than or equal to 5,000 lux, less than or equal to 1,000 lux, less than or equal to 500 lux, less than or equal to 100 lux, less than or equal to 50 lux, less than or equal to 10 lux, or less than or equal to 1 lux.

Figure 4:
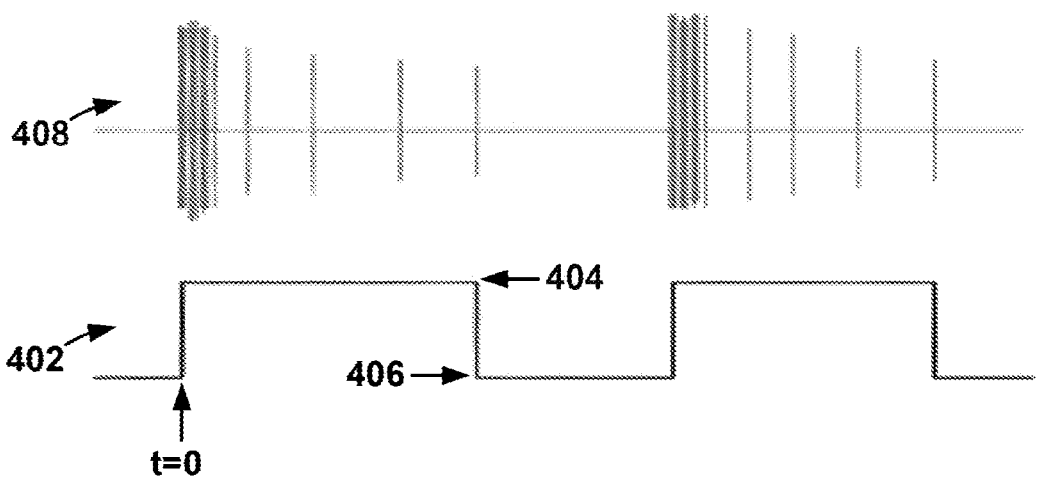
FIG. 4 illustrates ipRGC response to excitation of L-type and/or M-type cones.

In one example, the light source assembly 102 emits a second light having a luminous flux 402 as shown in FIG. 4. The luminous flux 402 has a peak intensity at a wavelength that is greater than or equal to 500 nm and less than or equal to 630 nm. The luminous flux 402 takes the form of a square wave that oscillates between a high level of luminous flux 404 and a low level of luminous flux 406. The low level of luminous flux 406 could be zero or near zero, but the low level of luminous flux 406 is generally less than the high level of luminous flux 404. The luminous flux 402 having a peak intensity at a wavelength between 500-630 nm primarily excites L-cones and M-cones within the retina, resulting in a response 408 of downstream ipRGCs. As shown, the response 408 is most frequent and intense immediately after the luminous flux 402 switches from the low level 406 to the high level 404 at t=0, for example. However, the response 408 continues at reduced intensity and frequency while the luminous flux 402 continues to be at the high level 404. The L-cones and M-cones become relatively inactive after the luminous flux 402 switches to the low level 406.

In short, high response intensity and high response frequencies for downstream ipRGCs occur in response to relatively quick positive changes (increases) in the luminous flux of the second light having a peak intensity between 500 and 630 nm. Although FIG. 4 shows the luminous flux 402 in the form of a square wave, waveforms such as a sinusoidal wave, a sawtooth wave, or a triangle wave can also exhibit relatively quick positive changes in luminous flux with peak intensity between 500 nm and 630, thereby efficiently exciting downstream ipRGCs.

In accordance with the method 200, the light source assembly 102 may include a first light source configured to emit the first light (e.g., luminous flux 302) and a second light source configured to emit the second light (e.g., luminous flux 402).

In various examples, the first luminous flux (e.g., luminous flux 302) is out of phase with the second luminous flux (e.g., luminous flux 402) by 180 degrees. Although less desirable, the phase difference between the first luminous flux and the second luminous flux could range anywhere from 0 to 180 degrees. In some embodiments, the first luminous flux will be at a maximum when the second luminous flux is at a minimum. In some embodiments, the first luminous flux will be at a minimum when the second luminous flux is at a maximum.

In various examples, the first luminous flux (e.g., luminous flux 302) and the second luminous flux (e.g., luminous flux 402) take the form of respective square waves with equal respective duty cycles or other waveforms having equal respective duty cycles. However, the first luminous flux and the second luminous flux can also take the form of respective square waves with unequal respective duty cycles or other waveforms having unequal respective duty cycles.

In various examples, the first luminous flux and the second luminous flux are periodic with respective oscillation frequencies that are less than or equal to 100 Hz. The first luminous flux and the second luminous flux may also be periodic with respective oscillation frequencies that are less than or equal to 50 Hz. The ipRGCs within the eye generally don't respond in synchrony with light that oscillates at frequencies greater than about 100 Hz.

In particular embodiments, at least 50%, at least 60%, at least 70%, at least 80%, at least 90% or at least 95% of a power spectral density of the second light corresponds to wavelengths within a range of 500 nm to 530 nm.

In particular embodiments, at least 50%, at least 60%, at least 70%, at least 80%, at least 90% or at least 95% of a power spectral density of the second light corresponds to wavelengths within a range of 530 nm to 560 nm.

In particular embodiments, at least 50%, at least 60%, at least 70%, at least 80%, at least 90% or at least 95% of a power spectral density of the second light corresponds to wavelengths within a range of 560 nm to 590 nm.

In particular embodiments, at least 50%, at least 60%, at least 70%, at least 80%, at least 90% or at least 95% of a power spectral density of the second light corresponds to wavelengths within a range of 590 nm to 630 nm.

In particular embodiments, the second luminous flux periodically reaches a minimum that is greater than zero.

In particular embodiments, the second luminous flux periodically reaches a minimum that is equal to zero.

Figure 5:
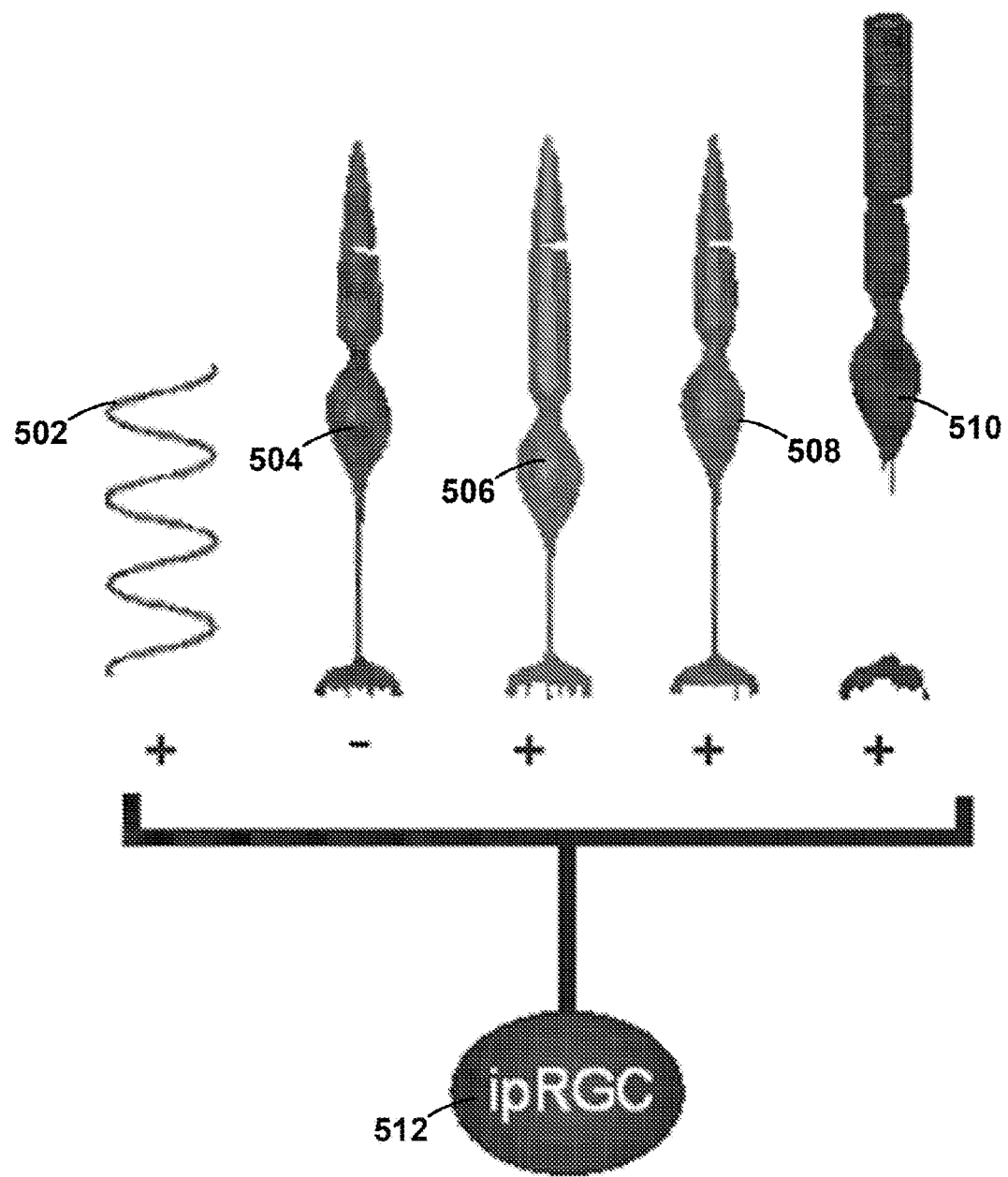
FIG. 5 illustrates ipRGC response to excitation of various types of upstream ganglion cells.

FIG. 5 illustrates ipRGC response to excitation of various types of upstream ganglion cells. As shown, ipRGCs 512 are stimulated by onset of blue light 502, red light 506, green light 508, and rod excitation 510. The ipRGCs 512 are stimulated by offset of violet light 504.

Figure 6:
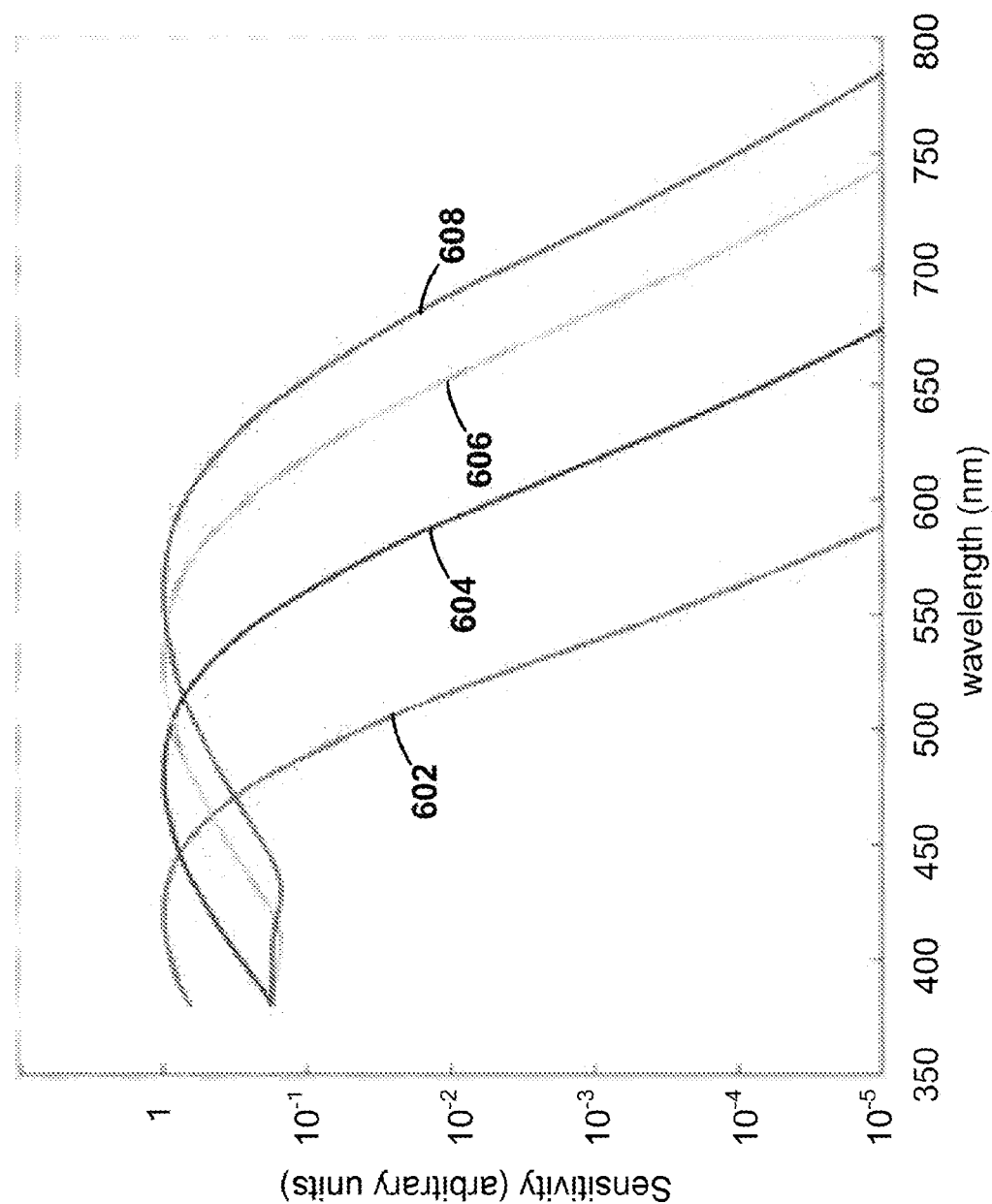
FIG. 6 includes photosensitivity curves of four types of ganglion cells in the eye.

FIG. 6 includes photosensitivity curves of four types of ganglion cells in the eye. The curve 602 represents S-cones, the curve 604 represents the melanopsin response of ipRGCs, the curve 606 represents M-cones, and the curve 608 represents L-cones.

Figure 7:
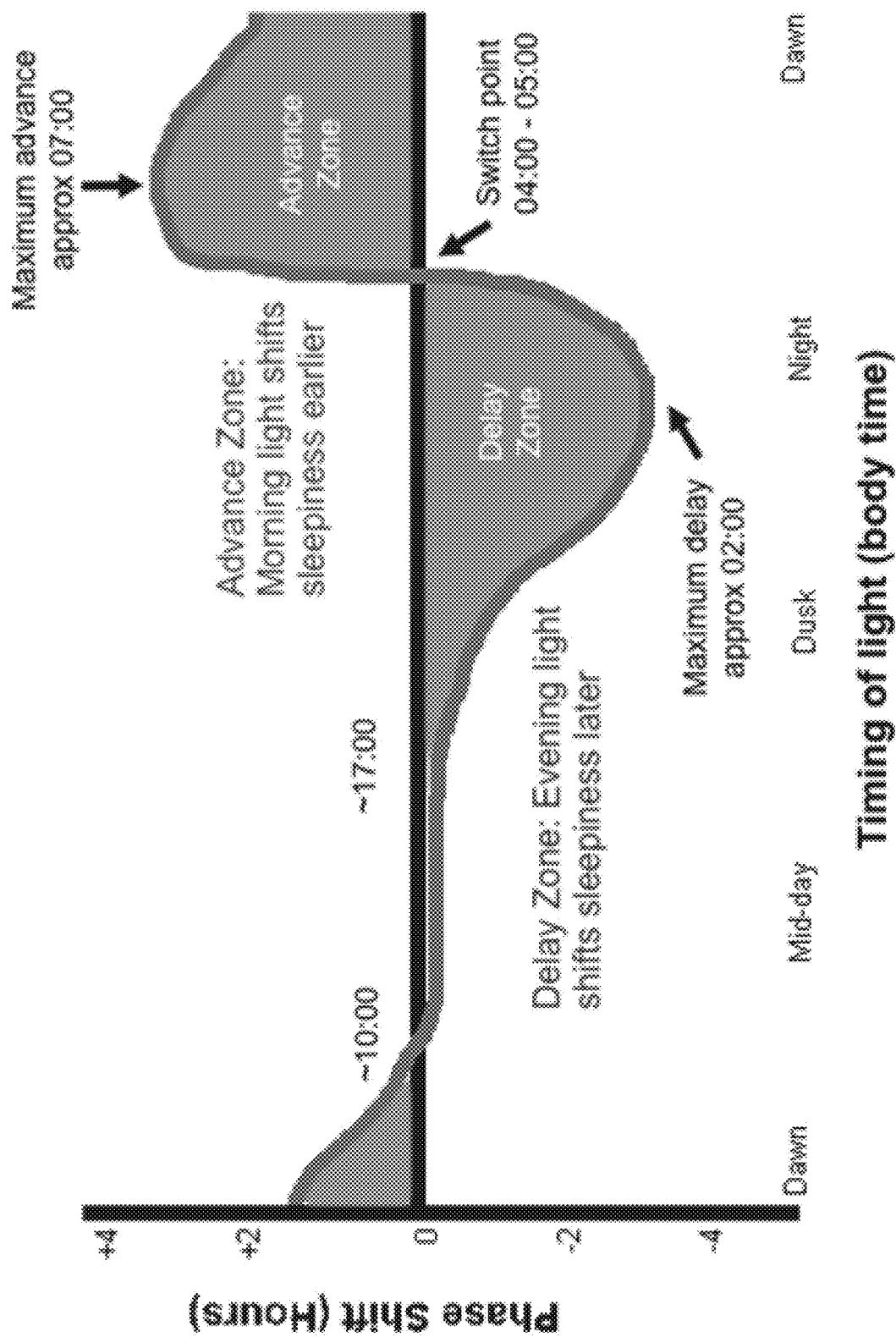
FIG. 7 illustrates the manipulation of circadian rhythm via retina illumination at varying times of day.
Figure 8:
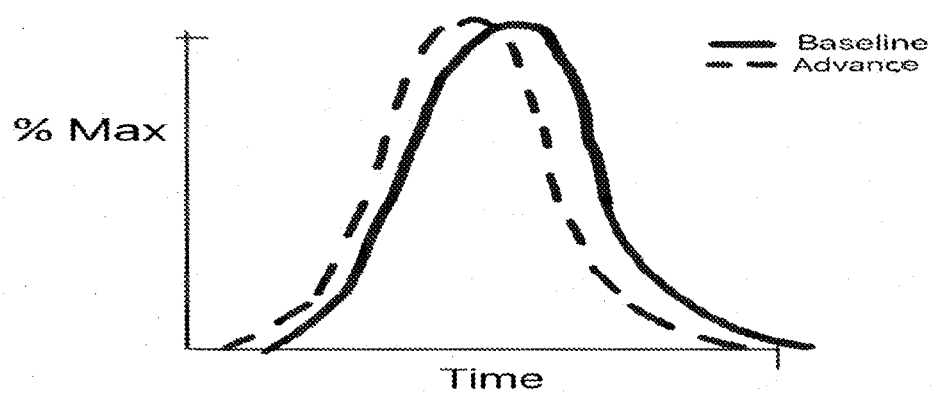
FIG. 8 illustrates an advancement of circadian rhythm.
Figure 9:
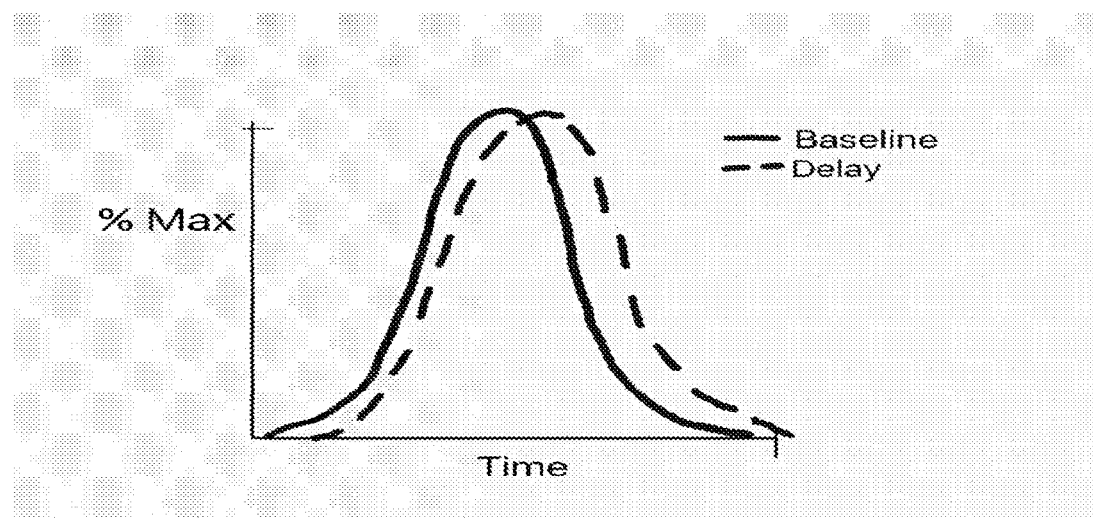
FIG. 9 illustrates a delay of circadian rhythm.

FIG. 7 illustrates the manipulation of circadian rhythm via retina illumination at varying times of day. The methods disclosed herein will have different effects depending on the time of day and/or the point at which the subject is currently at in their circadian rhythm. For a traditional circadian rhythm, the disclosed methods generally advance circadian rhythm when performed in the morning, and delay circadian rhythm when performed in the late afternoon or evening. As shown in FIG. 8, an "advancement" of circadian rhythm generally means one will become sleepy sooner. As shown in FIG. 9, "delay" of circadian rhythm generally means one will become sleepy later.

Figure 10:
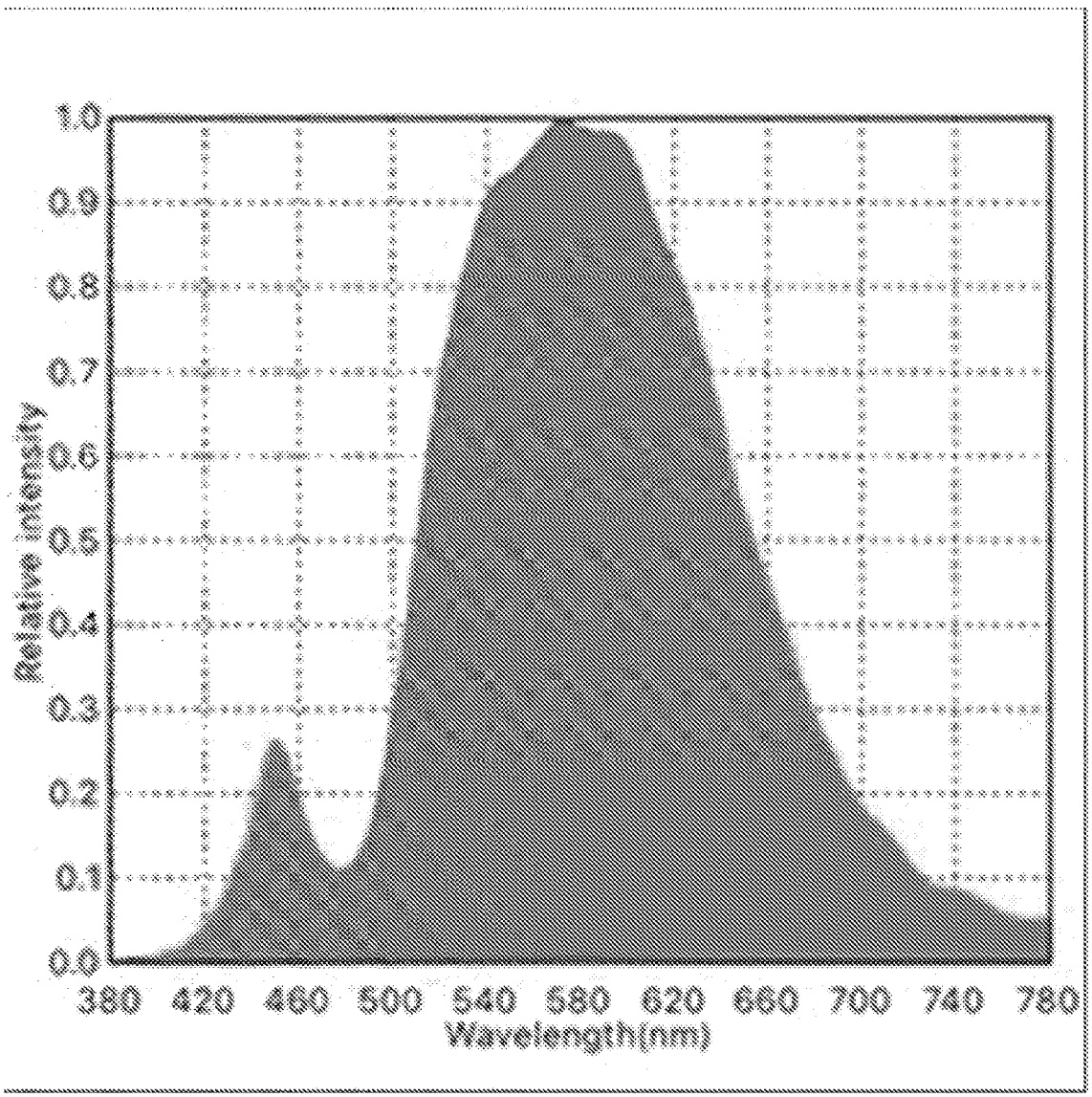
FIG. 10 illustrates an example intensity curve for a light source.

FIG. 10 illustrates an example intensity curve for a steady state "white" light source. As shown, the light source has a peak intensity around 570 nm.

Figure 11:
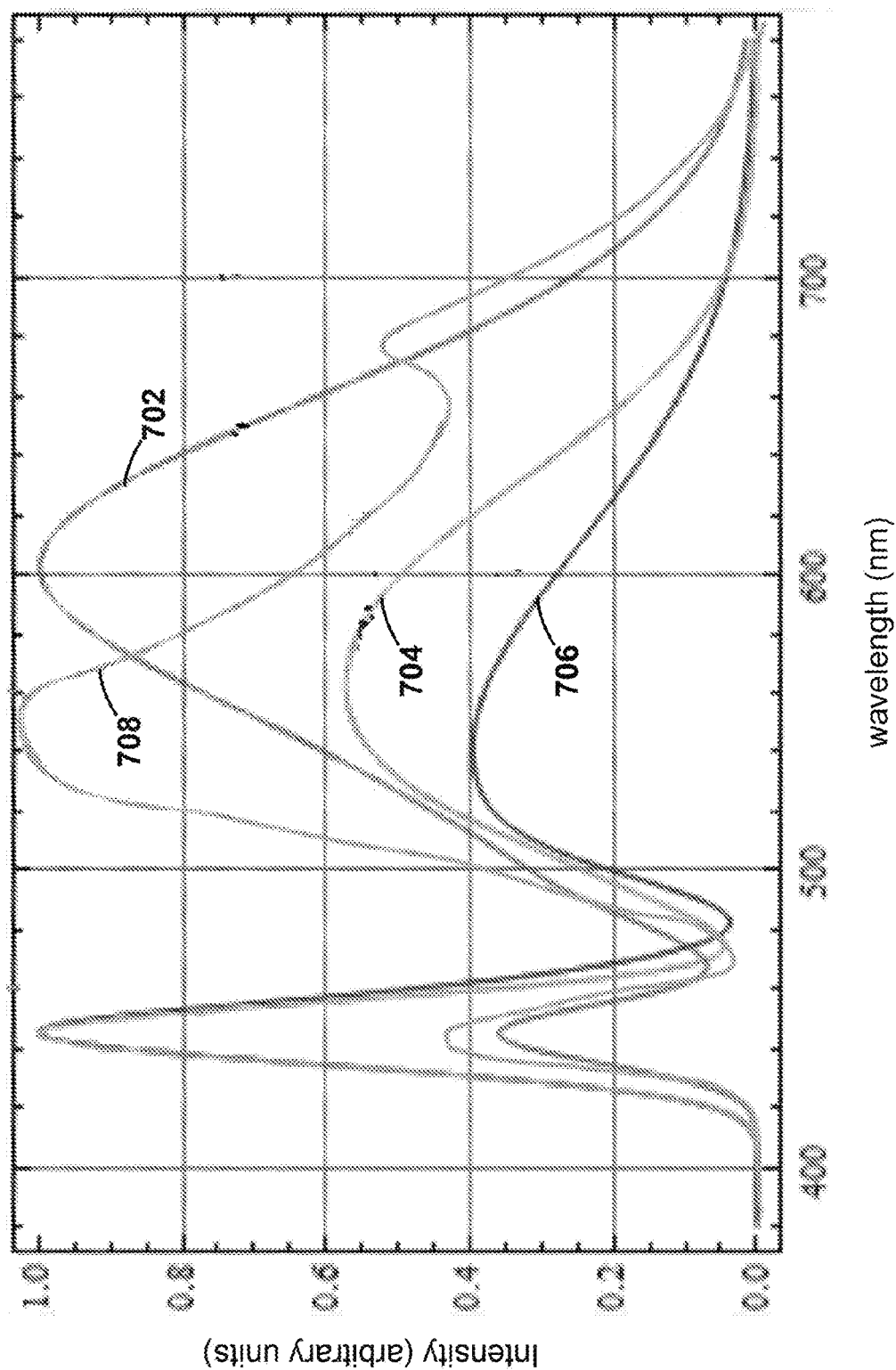
FIG. 11 illustrates example intensity curves for various types of light sources.

FIG. 11 illustrates example intensity curves for various types of light sources. Curve 702 is a "warm" white light source, curve 704 is a "neutral" white light source, and curve 706 is a "cool" white light source. The curve 708, in contrast to the other curves, exhibits a maximum intensity around 550 nm. Similar light sources might have a maximum at a wavelength anywhere from 520-570 nm.

Figure 12:
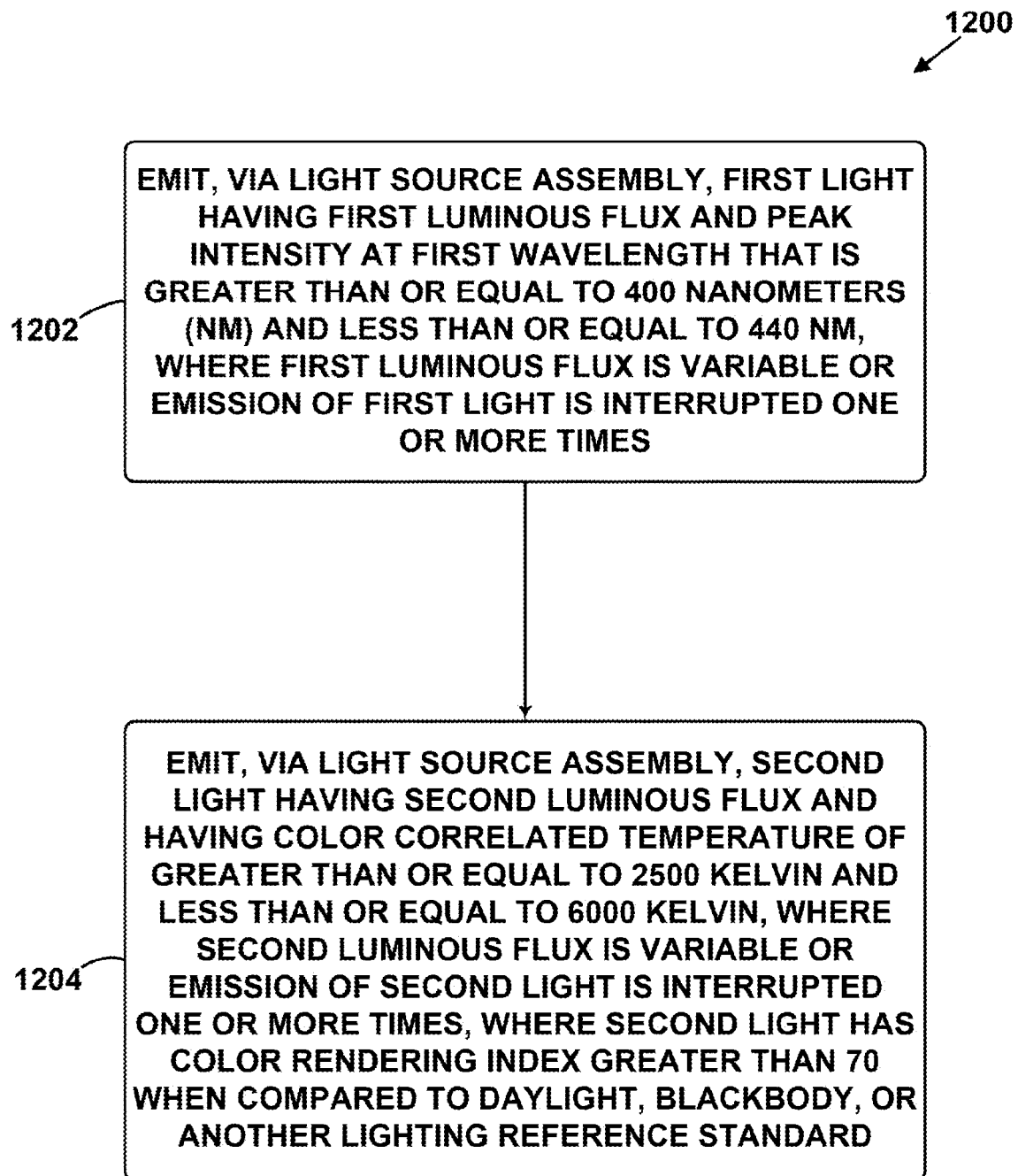
FIG. 12 is a block diagram of a method, according to an example embodiment.

FIG. 12 is a block diagram of a method 1200. The method 1200 and related methods disclosed herein can be performed to cause advancement or delay of a subject's circadian cycle for various purposes. Such methods can be performed to treat a subject afflicted with seasonal affective disorder (SAD) or another mood disorder, such as depression, bipolar disorder, or dysthymia. Disrupted or irregular sleep can also affect those suffering with cancer and/or heart disease, and these methods can be used accordingly to counteract such effects. The method 1200 may be performed with the device 100, for example.

At block 1202, the method 1200 includes emitting, via a light source assembly, a first light having a first luminous flux and a peak intensity at a first wavelength that is greater than or equal to 400 nanometers (nm) and less than or equal to 440 nm. The first luminous flux is variable or the emission of the first light is interrupted one or more times. For example, the light source assembly 102 may emit the first light in any manner described above with respect to block 202 or block 204 of the method 200.

At block 1204, the method 1200 includes emitting, via the light source assembly, a second light having a second luminous flux and having a color correlated temperature of greater than or equal to 2500 Kelvin and less than or equal to 6000 Kelvin. The second luminous flux is variable or the emission of the second light is interrupted one or more times. The second light has a color rendering index greater than 70 when compared to daylight, a blackbody, or another lighting reference standard. For example, the light source assembly 102 may emit the second light in any manner described above with respect to block 202 or block 204 of the method 200.

In various examples, the first light and/or the second light has an intensity spectrum that includes a finite range of wavelengths.

In some examples, the light source assembly includes a first light source configured to emit the first light and a second light source configured to emit the second light.

In particular examples, the light source assembly includes one or more light emitting diodes (LEDs).

In certain examples, the first luminous flux is out of phase with the second luminous flux by 180 degrees.

In some embodiments, the first luminous flux will be at a maximum when the second luminous flux is at a minimum. In some embodiments, the first luminous flux will be at a minimum when the second luminous flux is at a maximum.

In some examples, the first luminous flux and/or the second luminous flux takes the form of a square wave, a sinusoidal wave, a sawtooth wave, or a triangle wave.

In certain examples, the first luminous flux and the second luminous flux take the form of respective square waves with equal or unequal respective duty cycles or other waveforms having equal or unequal respective duty cycles.

In particular examples, the first luminous flux and the second luminous flux are periodic with respective frequencies that are less than or equal to 100 Hz or are less than or equal to 50 Hz.

In certain examples, emitting the first light and/or the second light includes emitting the first light and/or the second light such that the first light and/or the second light respectively illuminates a retina of a user with an illuminance that is less than or equal to 10,000 lux, less than or equal to 5,000 lux, less than or equal to 1,000 lux, less than or equal to 500 lux, less than or equal to 100 lux, less than or equal to 50 lux, less than or equal to 10 lux, or less than or equal to 1 lux.

In particular embodiments, the first luminous flux periodically reaches a minimum that is greater than zero.

In particular embodiments, the first luminous flux periodically reaches a minimum that is equal to zero.

Additional examples include a plurality of light sources (e.g., light emitting diodes) configured to emit light having a peak wavelength within a range of 400 nm to 440 nm. In particular examples, the plurality of light sources are configured to emit respective ranges of wavelengths of light that are different from each other (e.g., overlapping but non-identical). Additionally, the plurality of light sources may be configured to collectively emit white light having a color rendering index of greater than 70 as compared to daylight, a blackbody, or another lighting reference standard.

Additional examples include a white light source having a color rendering index of greater than 70 as compared to daylight, a blackbody, or another lighting reference standard. The white light source is configured to emit light with a peak wavelength within a range of 400 nm to 440 nm.

Any of the devices or light sources described herein may be incorporated into a wearable device, including but not limited to goggles, a headband, armwear, wristwear, or a therapeutic wearable device configured to shine light onto a subject's retina.

Any of the devices or light sources described herein may be incorporated into a vehicle including but not limited to an automobile, an airplane, a helicopter, a boat, a ship, or a train.

Any of the devices or light sources described herein may be incorporated into a dashboard, an accent lighting unit, a cabin general lighting unit, or a headlight unit.

Any of the devices or light sources described herein may be incorporated into a display unit, including but not limited to a cell phone, a tablet computer, a monitor, or a television.

Any of the devices or light sources described herein may be incorporated into a lighting unit including but not limited to a lamp, a nightlight, a chandelier, or an overhead lighting unit.

Figure 13:
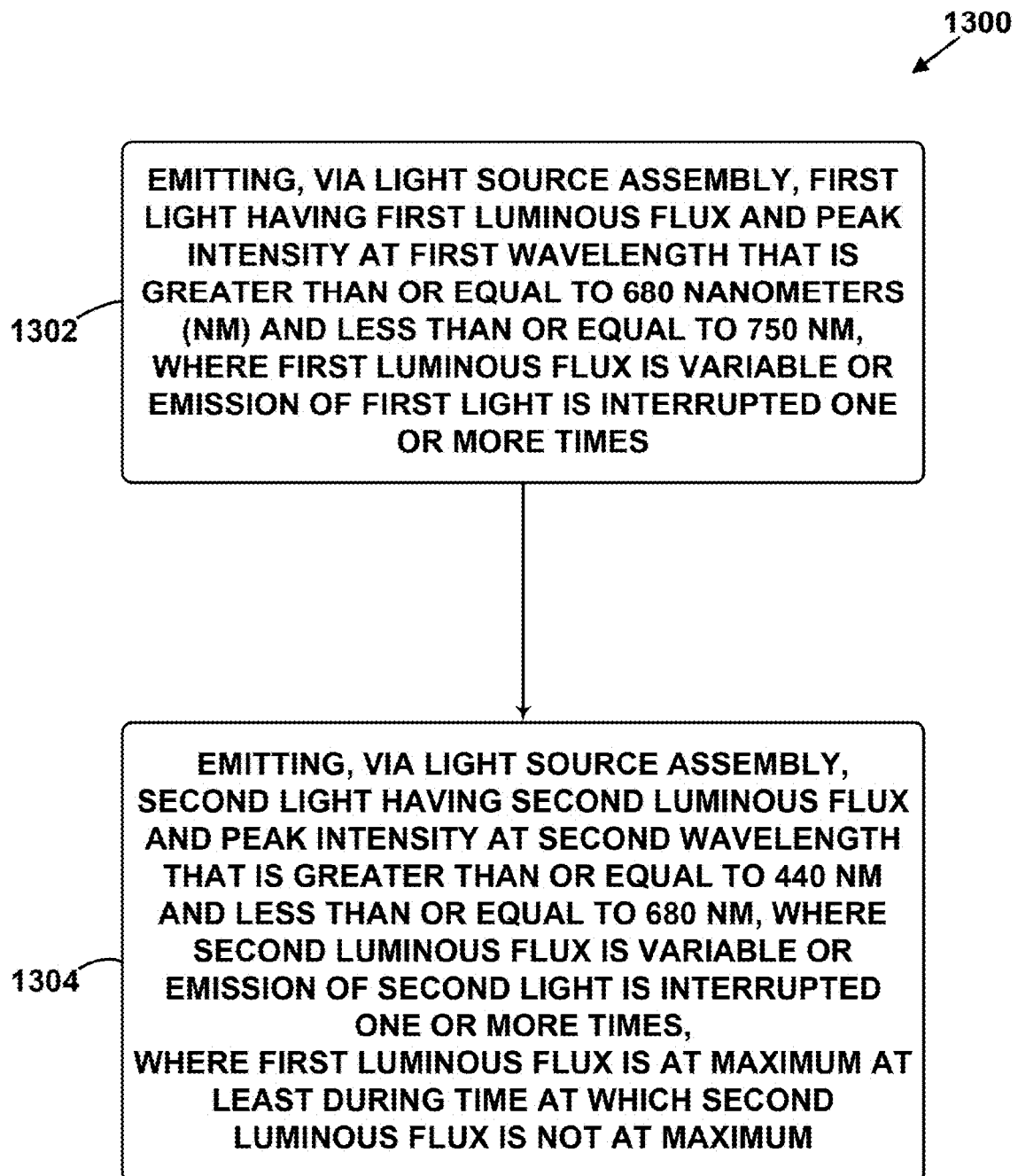
FIG. 13 is a block diagram of a method, according to an example embodiment.

FIG. 13 is a block diagram of a method 1300. The method 1300 and related methods disclosed herein can be performed to cause advancement or delay of a subject's circadian cycle for various purposes. Such methods can be performed to treat a subject afflicted with seasonal affective disorder (SAD) or another mood disorder, such as depression, bipolar disorder, or dysthymia. Disrupted or irregular sleep can also affect those suffering with cancer and/or heart disease, and these methods can be used accordingly to counteract such effects.

At block 1302, the method 1300 includes emitting, via a light source assembly, a first light having a first luminous flux and a peak intensity at a first wavelength that is greater than or equal to 680 nanometers (nm) and less than or equal to 750 nm. In other words, the first light may be most intense (or have a local maximum) at a wavelength that is greater than or equal to 680 nm and less than or equal to 750 nm. More specifically, the first wavelength may be greater than or equal to 680 nm and less than or equal to 695 nm, greater than or equal to 695 nm and less than or equal to 720 nm, or greater than or equal to 720 nm and less than or equal to 750 nm.

In this context, the first luminous flux is variable or the emission of the first light is interrupted one or more times. For example, the first luminous flux may take the form of a square wave, a sinusoidal wave, a sawtooth wave, a triangle wave, or any other digital or analog wave. Other examples are possible.

The first light may be emitted by the light source assembly 102 such that the first light illuminates a retina of a user with an illuminance that is less than or equal to 10,000 lux, less than or equal to 5,000 lux, less than or equal to 1,000 lux, less than or equal to 500 lux, less than or equal to 100 lux, less than or equal to 50 lux, less than or equal to 10 lux, or less than or equal to 1 lux.

In one example, the light source assembly 102 emits a first light having a luminous flux 402 as shown in FIG. 4. The luminous flux 402 has a peak intensity at a wavelength that is greater than or equal to 680 nm and less than or equal to 750 nm. The luminous flux 402 takes the form of a square wave that oscillates between a high level of luminous flux 404 and a low level of luminous flux 406. The low level of luminous flux 406 could be zero or near zero, but the low level of luminous flux 406 is generally less than the high level of luminous flux 404. The luminous flux 402 having a peak intensity at a wavelength between 680-750 nm primarily excites L-cones within the retina, resulting in a response 408 of downstream ipRGCs. As shown, the response 408 is most frequent and intense immediately after the luminous flux 402 switches from the low level 406 to the high level 404 at t=0, for example. However, the response 408 continues at reduced intensity and frequency while the luminous flux 402 continues to be at the high level 404. The L-cones become relatively inactive after the luminous flux 402 switches to the low level 406.

In short, high response intensity and high response frequencies for downstream ipRGCs occur in response to relatively quick positive changes (increases) in the luminous flux of the first light having a peak intensity between 680 and 750 nm. Although FIG. 4 shows the luminous flux 402 in the form of a square wave, waveforms such as a sinusoidal wave, a sawtooth wave, or a triangle wave can also exhibit relatively quick positive changes in luminous flux with peak intensity between 680 nm and 750, thereby efficiently exciting downstream ipRGCs.

In particular embodiments, at least 50%, at least 60%, at least 70%, at least 80%, at least 90% or at least 95% of a power spectral density of the first light corresponds to wavelengths within a range of 680 nm to 695 nm.

In particular embodiments, at least 50%, at least 60%, at least 70%, at least 80%, at least 90% or at least 95% of a power spectral density of the first light corresponds to wavelengths within a range of 695 nm to 720 nm.

In particular embodiments, at least 50%, at least 60%, at least 70%, at least 80%, at least 90% or at least 95% of a power spectral density of the first light corresponds to wavelengths within a range of 720 nm to 750 nm.

In particular embodiments, the first luminous flux periodically reaches a minimum that is greater than zero.

In particular embodiments, the first luminous flux periodically reaches a minimum that is equal to zero.

At block 1304, the method 1300 includes emitting, via the light source assembly, a second light having a second luminous flux and a peak intensity at a second wavelength that is less than or equal to 680 nm. In other words, the second light may be most intense (or have a local maximum) at a wavelength that is greater than or equal to 440 nm and less than or equal to 680 nm. More specifically, the second wavelength may be greater than or equal to 440 nm and less than or equal to 520 nm, greater than or equal to 520 nm and less than or equal to 600 nm, or greater than or equal to 600 nm and less than or equal to 680 nm.

In this context, the second luminous flux is variable or the emission of the second light is interrupted one or more times. For example, the second luminous flux may take the form of a square wave, a sinusoidal wave, a sawtooth wave, a triangle wave, or any other digital or analog wave. Other examples are possible.

The second light may be emitted by the light source assembly 102 such that the second light illuminates a retina of a user with an illuminance that is less than or equal to 10,000 lux, less than or equal to 5,000 lux, less than or equal to 1,000 lux, less than or equal to 500 lux, less than or equal to 100 lux, less than or equal to 50 lux, less than or equal to 10 lux, or less than or equal to 1 lux.

In one example, the light source assembly 102 emits a second light having a luminous flux 302 as shown in FIG. 3. The luminous flux 302 has a peak intensity at a wavelength that is greater than or equal to 440 nm and less than or equal to 680 nm. The luminous flux 302 takes the form of a square wave that oscillates between a high level of luminous flux 304 and a low level of luminous flux 306. The low level of luminous flux 306 could be zero or near zero, but the low level of luminous flux 306 is generally less than the high level of luminous flux 304. In this context, one purpose of the second light is to provide a contrast balance with respect to the first light. That is, the first light having a peak wavelength between 680 and 750 nm can be used to advance or delay circadian rhythm in a subject, while the second light balances against the first light such that the subject perceives little or no variation in light intensity. In some examples, the first light might penetrate a subject's eyelids while the subject is sleeping. By further example, the light source assembly 102 might be operated in a setting that is substantially void of ambient light (e.g., has less than 10 lux of ambient light).

In accordance with the method 1300, the light source assembly 102 may include a first light source configured to emit the first light (e.g., luminous flux 402) and a second light source configured to emit the second light (e.g., luminous flux 302).

In various examples, the first luminous flux (e.g., luminous flux 402) is out of phase with the second luminous flux (e.g., luminous flux 302) by 180 degrees. Although less desirable, the phase difference between the first luminous flux and the second luminous flux could range anywhere from 0 to 180 degrees.

In some embodiments, the first luminous flux will be at a maximum when the second luminous flux is at a minimum. In some embodiments, the first luminous flux will be at a minimum when the second luminous flux is at a maximum.

In various examples, the first luminous flux (e.g., luminous flux 402) and the second luminous flux (e.g., luminous flux 302) take the form of respective square waves with equal respective duty cycles or other waveforms having equal respective duty cycles. However, the first luminous flux and the second luminous flux can also take the form of respective square waves with unequal respective duty cycles or other waveforms having unequal respective duty cycles.

In various examples, the first luminous flux and the second luminous flux are periodic with respective oscillation frequencies that are less than or equal to 100 Hz. The first luminous flux and the second luminous flux may also be periodic with respective oscillation frequencies that are less than or equal to 50 Hz.

In particular embodiments, at least 50%, at least 60%, at least 70%, at least 80%, at least 90% or at least 95% of a power spectral density of the second light corresponds to wavelengths within a range of 440 nm to 680 nm.

In particular embodiments, at least 50%, at least 60%, at least 70%, at least 80%, at least 90% or at least 95% of a power spectral density of the second light corresponds to wavelengths within a range of 440 nm to 520 nm.

In particular embodiments, at least 50%, at least 60%, at least 70%, at least 80%, at least 90% or at least 95% of a power spectral density of the second light corresponds to wavelengths within a range of 520 nm to 600 nm.

In particular embodiments, at least 50%, at least 60%, at least 70%, at least 80%, at least 90% or at least 95% of a power spectral density of the second light corresponds to wavelengths within a range of 600 nm to 680 nm.

In particular embodiments, the second luminous flux periodically reaches a minimum that is greater than zero.

In particular embodiments, the second luminous flux periodically reaches a minimum that is equal to zero.

Figure 14:
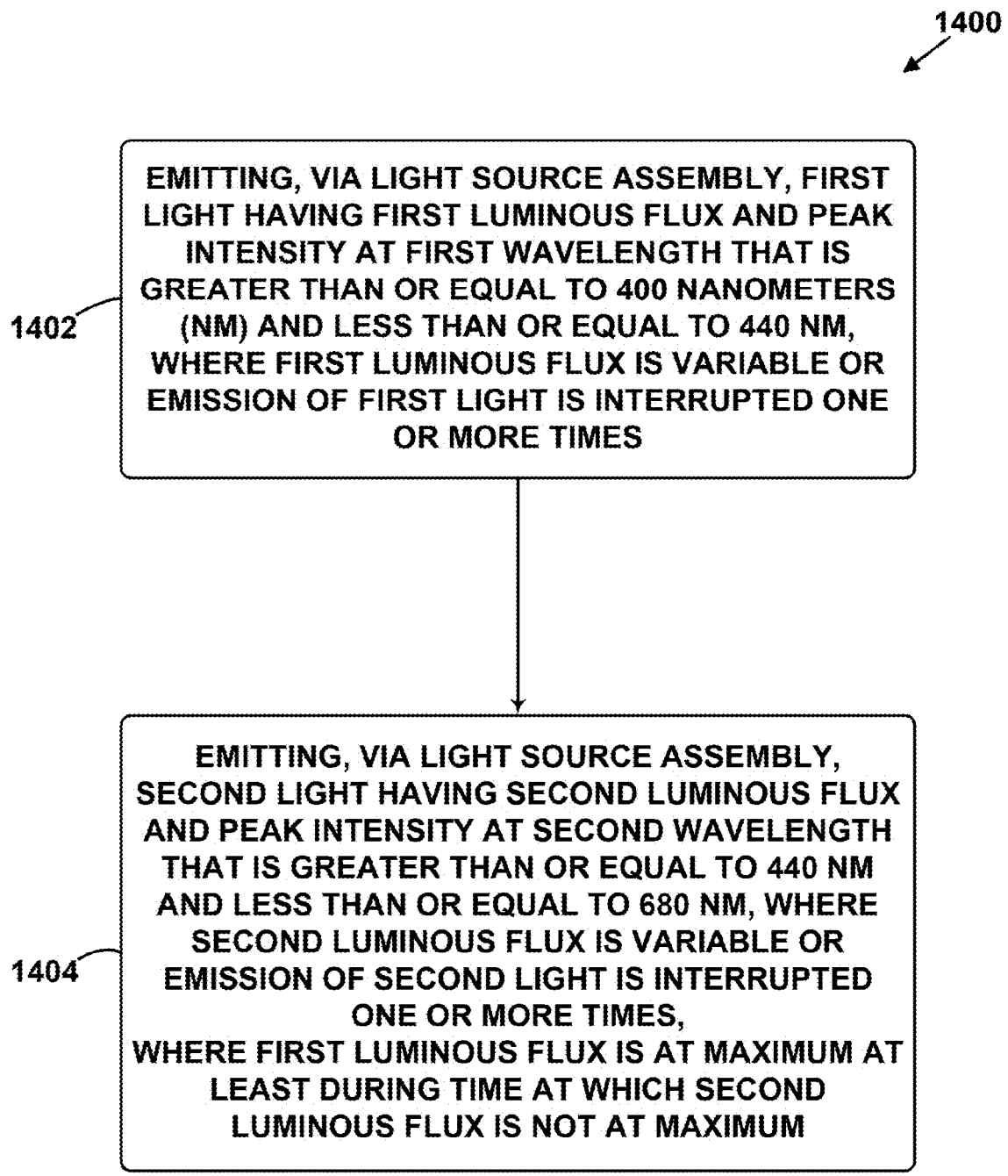
FIG. 14 is a block diagram of a method, according to an example embodiment.

FIG. 14 is a block diagram of a method 1400. The method 1400 and related methods disclosed herein can be performed to cause advancement or delay of a subject's circadian cycle for various purposes. Such methods can be performed to treat a subject afflicted with seasonal affective disorder (SAD) or another mood disorder, such as depression, bipolar disorder, or dysthymia. Disrupted or irregular sleep can also affect those suffering with cancer and/or heart disease, and these methods can be used accordingly to counteract such effects.

At block 1402, the method 1400 includes emitting, via a light source assembly, a first light having a first luminous flux and a peak intensity at a first wavelength that is greater than or equal to 400 nanometers (nm) and less than or equal to 440 nm. In other words, the first light may be most intense (or have a local maximum) at a wavelength that is greater than or equal to 400 nm and less than or equal to 440 nm. More specifically, the first wavelength may be greater than or equal to 400 nm and less than or equal to 415 nm, greater than or equal to 415 nm and less than or equal to 430 nm, or greater than or equal to 430 nm and less than or equal to 440 nm.

In this context, the first luminous flux is variable or the emission of the first light is interrupted one or more times. For example, the first luminous flux may take the form of a square wave, a sinusoidal wave, a sawtooth wave, a triangle wave, or any other digital or analog wave. Other examples are possible.

The first light may be emitted by the light source assembly 102 such that the first light illuminates a retina of a user with an illuminance that is less than or equal to 10,000 lux, less than or equal to 5,000 lux, less than or equal to 1,000 lux, less than or equal to 500 lux, less than or equal to 100 lux, less than or equal to 50 lux, less than or equal to 10 lux, or less than or equal to 1 lux.

In one example, the light source assembly 102 emits a first light having a luminous flux 302 as shown in FIG. 3. The luminous flux 302 has a peak intensity at a wavelength that is greater than or equal to 400 nm and less than or equal to 440 nm. The luminous flux 302 takes the form of a square wave that oscillates between a high level of luminous flux 304 and a low level of luminous flux 306. The low level of luminous flux 306 could be zero or near zero, but the high level of luminous flux 306 is generally less than the high level of luminous flux 304. The luminous flux 302 having a peak intensity at a wavelength between 400-440 nm primarily (e.g., upon turn off) excites S-cones within the retina, resulting in a response 308 of downstream ipRGCs. As shown, the response 308 is most frequent and intense immediately after the luminous flux 302 switches from the high level 304 to the low level 306 at t=0, for example. However, the response 308 continues at reduced intensity and frequency while the luminous flux 302 continues to be at the low level 306. The S-cones become relatively inactive after the luminous flux 302 switches to the high level 304.

In short, high response intensity and high response frequencies for downstream ipRGCs occur in response to relatively quick negative changes (decreases) in the luminous flux of the first light having a peak intensity between 400 and 440 nm. Although FIG. 3 shows the luminous flux 302 in the form of a square wave, waveforms such as a sinusoidal wave, a sawtooth wave, or a triangle wave can also exhibit relatively quick negative changes in luminous flux with peak intensity between 400 nm and 440 nm, thereby efficiently exciting downstream ipRGCs.

In particular embodiments, at least 50%, at least 60%, at least 70%, at least 80%, at least 90% or at least 95% of a power spectral density of the first light corresponds to wavelengths within a range of 400 nm to 415 nm.

In particular embodiments, at least 50%, at least 60%, at least 70%, at least 80%, at least 90% or at least 95% of a power spectral density of the first light corresponds to wavelengths within a range of 415 nm to 430 nm.

In particular embodiments, at least 50%, at least 60%, at least 70%, at least 80%, at least 90% or at least 95% of a power spectral density of the first light corresponds to wavelengths within a range of 430 nm to 440 nm.

In particular embodiments, the first luminous flux periodically reaches a minimum that is greater than zero.

In particular embodiments, the first luminous flux periodically reaches a minimum that is equal to zero.

At block 1404, the method 1400 includes emitting, via the light source assembly, a second light having a second luminous flux and a peak intensity at a second wavelength that is greater than or equal to 440 nm and less than or equal to 680 nm. In other words, the second light may be most intense (or have a local maximum) at a wavelength that is greater than or equal to 440 nm and less than or equal to 680 nm. More specifically, the second wavelength may be greater than or equal to 440 nm and less than or equal to 520 nm, greater than or equal to 520 nm and less than or equal to 600 nm, or greater than or equal to 600 nm and less than or equal to 680 nm.

In this context, the second luminous flux is variable or the emission of the second light is interrupted one or more times. For example, the second luminous flux may take the form of a square wave, a sinusoidal wave, a sawtooth wave, a triangle wave, or any other digital or analog wave. Other examples are possible.

The second light may be emitted by the light source assembly 102 such that the second light illuminates a retina of a user with an illuminance that is less than or equal to 10,000 lux, less than or equal to 5,000 lux, less than or equal to 1,000 lux, less than or equal to 500 lux, less than or equal to 100 lux, less than or equal to 50 lux, less than or equal to 10 lux, or less than or equal to 1 lux.

In one example, the light source assembly 102 emits a second light having a luminous flux 402 as shown in FIG. 4. The luminous flux 402 has a peak intensity at a wavelength that is greater than or equal to 440 nm and less than or equal to 680 nm. The luminous flux 402 takes the form of a square wave that oscillates between a high level of luminous flux 404 and a low level of luminous flux 406. The low level of luminous flux 406 could be zero or near zero, but the low level of luminous flux 406 is generally less than the high level of luminous flux 404. In this context, one purpose of the second light is to provide a contrast balance with respect to the first light. That is, the first light having a peak wavelength between 400 and 440 nm can be used (e.g., as part of a wearable device) to advance or delay circadian rhythm in a subject, while the second light balances against the first light such that the subject perceives little or no variation in light intensity.

In accordance with the method 1400, the light source assembly 102 may include a first light source configured to emit the first light (e.g., luminous flux 302) and a second light source configured to emit the second light (e.g., luminous flux 402).

In various examples, the first luminous flux (e.g., luminous flux 302) is out of phase with the second luminous flux (e.g., luminous flux 402) by 180 degrees. Although less desirable, the phase difference between the first luminous flux and the second luminous flux could range anywhere from 0 to 180 degrees. In some embodiments, the first luminous flux will be at a maximum when the second luminous flux is at a minimum. In some embodiments, the first luminous flux will be at a minimum when the second luminous flux is at a maximum.

In various examples, the first luminous flux (e.g., luminous flux 302) and the second luminous flux (e.g., luminous flux 402) take the form of respective square waves with equal respective duty cycles or other waveforms having equal respective duty cycles. However, the first luminous flux and the second luminous flux can also take the form of respective square waves with unequal respective duty cycles or other waveforms having unequal respective duty cycles.

In various examples, the first luminous flux and the second luminous flux are periodic with respective oscillation frequencies that are less than or equal to 100 Hz. The first luminous flux and the second luminous flux may also be periodic with respective oscillation frequencies that are less than or equal to 50 Hz.

In particular embodiments, at least 50%, at least 60%, at least 70%, at least 80%, at least 90% or at least 95% of a power spectral density of the second light corresponds to wavelengths within a range of 440 nm to 680 nm.

In particular embodiments, at least 50%, at least 60%, at least 70%, at least 80%, at least 90% or at least 95% of a power spectral density of the second light corresponds to wavelengths within a range of 440 nm to 520 nm.

In particular embodiments, at least 50%, at least 60%, at least 70%, at least 80%, at least 90% or at least 95% of a power spectral density of the second light corresponds to wavelengths within a range of 520 nm to 600 nm.

In particular embodiments, at least 50%, at least 60%, at least 70%, at least 80%, at least 90% or at least 95% of a power spectral density of the second light corresponds to wavelengths within a range of 600 nm to 680 nm.

In particular embodiments, the second luminous flux periodically reaches a minimum that is greater than zero.

In particular embodiments, the second luminous flux periodically reaches a minimum that is equal to zero.

In particular embodiments, the second light has a color rendering index of greater than 70 as compared to daylight, a blackbody, or another lighting reference standard.

Figure 15:
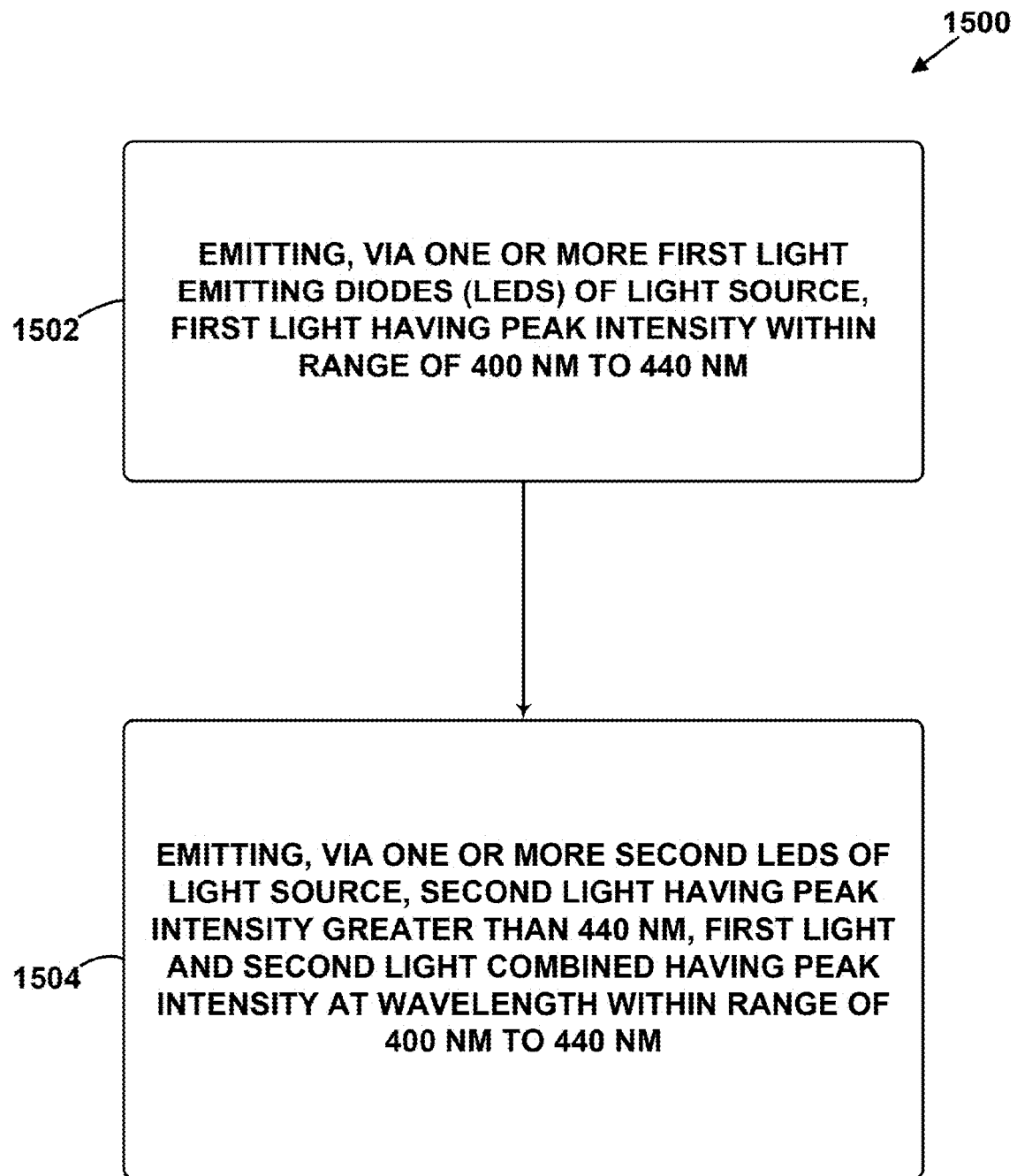
FIG. 15 is a block diagram of a method, according to an example embodiment.

FIG. 15 is a block diagram of a method 1500. The method 1500 and related methods disclosed herein can be performed to help prevent changes (e.g., time shifts) to a subject's circadian cycle for various purposes. Such methods can be performed to treat a subject afflicted with seasonal affective disorder (SAD) or another mood disorder, such as depression, bipolar disorder, or dysthymia. Disrupted or irregular sleep can also affect those suffering with cancer and/or heart disease, and these methods can be used accordingly to counteract such effects.

At block 1502, the method 1500 includes emitting, via one or more first light emitting diodes (LEDs) of a light source, first light having a peak intensity within a range of 400 nm to 440 nm. In other words, the first light may be most intense (or have a local maximum) at a wavelength that is greater than or equal to 400 nm and less than or equal to 440 nm. More specifically, the first wavelength may be greater than or equal to 400 nm and less than or equal to 415 nm, greater than or equal to 415 nm and less than or equal to 430 nm, or greater than or equal to 430 nm and less than or equal to 440 nm.

The one or more first LEDs that emit the first light may be part of the light source 102, for example.

In particular embodiments, at least 50%, at least 60%, at least 70%, at least 80%, at least 90% or at least 95% of a power spectral density of the first light corresponds to wavelengths within a range of 400 nm to 440 nm.

In particular embodiments, at least 50%, at least 60%, at least 70%, at least 80%, at least 90% or at least 95% of a power spectral density of the first light corresponds to wavelengths within a range of 400 nm to 415 nm.

In particular embodiments, at least 50%, at least 60%, at least 70%, at least 80%, at least 90% or at least 95% of a power spectral density of the first light corresponds to wavelengths within a range of 415 nm to 430 nm.

In particular embodiments, at least 50%, at least 60%, at least 70%, at least 80%, at least 90% or at least 95% of a power spectral density of the first light corresponds to wavelengths within a range of 430 nm to 440 nm.

At block 1504, the method 1500 includes emitting, via one or more second LEDs of the light source, second light having a peak intensity within a range of 400 nm to 440 nm. In this context, the first light and the second light combined have a peak intensity at a wavelength within a range of 400 nm to 440 nm.

In particular embodiments, the second light has a color rendering index higher than 70 when compared to daylight, a blackbody, or another lighting reference standard.

The method 1500 and related devices might be useful in the context of street lighting, dashboard lighting, accent lighting, cabin general lighting unit, or headlights, as the (e.g, steady, non-oscillatory) first light having the peak intensity between 400 to 440 nm will generally inhibit changes in a subject's circadian rhythm. For example, the first light might have a substantially constant intensity that does not vary by more than 5-10% over time.

Additional Examples

The following includes further details related to the methods and systems described above.

Method for increasing efficacy of intrinsically photosensitive retinal ganglion cell activity in humans by targeting upstream retinal circuitry Within examples, a light source temporospectrally modulates such to excite intrinsically photosensitive retinal ganglion cells (ipRGCs) in the eye which project to circadian rhythm centers in the brain. Specific wavelengths and temporal sequences of lights are presented to drive spectrally opponent inputs from signals originating in the cone photoreceptors to ipRGCs which project to brain centers involved in non-image forming vision and mediate functions related to circadian rhythms, arousal and sleep. Light stimuli described in this disclosure are presented by themselves or superimposed over ambient light to with the aim of affecting the circadian pathway. The aim of some of the methods disclosed herein is to synchronize, advance, and/or delay the internal phase of a human circadian activity rhythm and modulate arousal and sleep with the use of low light intensities and particular wavelengths.

The aim of the disclosed methods is to cause delays or advances in circadian rhythm to help an individual synchronize circadian rhythmicity by resetting circadian phase. This may enable better preparation for time zone shifts to alleviate jet lag, preparation for non-traditional work shifts or sudden changes in work habit, staying alert for driving late into the evening, delivering therapy for seasonal affect disorder, better maintaining normal regular sleep-wake cycles in adults, children, and infants, better timing of peak mental, emotional, and physical performance, and other similar benefits. Previous methods use bright (e.g., 10,000 lux) steady state white, or bright blue (e.g. dominant wavelength ~480 nm lights), bright steady-state lights containing RGB primary LEDs that can be controlled individually to match natural scenes, or steady-state LED lights that contain specific wavelengths. Previous references purport to explain the direct effect of changing melatonin levels on circadian rhythm. While exciting the circadian pathway via modulation of upstream cones or ipRGCs does suppress the production of melatonin in the body, melatonin is merely a marker of circadian phase, and there is no evidence that it can influence the circadian rhythm. Therefore, indirect suppression of melatonin production is possible, but there is no evidence to support claims that melatonin affects the circadian rhythm.

Examples include a spectorotemporal light source designed to stimulate ipRGCs by capitalizing on their spectrally opponent response properties. Inputs from long wavelength sensitive (L-) and middle wavelength sensitive (M-) cones excite ipRGCs, and inputs from short wavelength sensitive (S-) cone photoreceptors inhibit them. IpRGCs are extremely sensitive to lights in the 500 nm-630 nm wavelength range that are absorbed by the L/M cones. However, their responses to steady L/M cone stimulation are transient such that driving cone based responses in ipRGCs with a temporally modulated spectrally opponent stimulus that alternately stimulates S cones and L/M cones may be useful. Lights that stimulate S-cones drive responses in ipRGCs at their offset and lights that stimulate L/M cones drive ipRGCs at their onset. Thus, stimuli that combine offset of S-cone stimuli followed by the onset of L/M cone stimuli are capable of driving ipRGCs with low light intensities. A light producing alternating S-cone and L/M cone stimulation can produce strong continuous activity in the ipRGCs.

The ipRGC, in turn, send their axons to the suprachiasmatic nuclei (SCN), the circadian master clock in the brain, the pregeniculate nucleus (PGN) and other centers involved in arousal and sleep. Since cone driven responses have different temporal characteristics, spectral tuning and sensitivity than responses that are driven by the intrinsic photosensitivity of the ipRGCs, the disclosed methods use specific wavelengths (or wavebands) and temporal sequences to drive ipRGC responses at light levels as much as 1,000 times lower than those required to drive them by stimulating their intrinsic photo-response. Because the upstream cone photoreceptors effectively respond to lower light intensities via gain mechanisms, the stimulated ipRGCs send robust signals to the brain capable of synchronizing circadian rhythm within the human body.

Examples include the subsequent applications such as a luminaire, personal lighting device, or transportation cabin light.

Circadian rhythm is reference to an internal clock that governs sleep and awake cycles, whereas circadian rhythmicity includes sleep, physical activity, alertness, hormone levels, body temperature, immune function, and digestive activity. Circadian rhythm is controlled by the suprachiasmatic nucleus (SCN), which serves as the body's "master clock." The SCN synchronizes rhythms across the entire body, and circadian rhythmicity is lost if SCN function is disrupted or destroyed. The SCN maintains control across the body by synchronizing slave oscillators, which exhibit their own near-24-hour rhythms and subsequently control circadian phenomena in local tissue. Synchronization of this internal clock to the external Earth-based 24-hour cycle will be referred to herein as circadian entrainment.

Given the SCN in the hypothalamus acts as the master clock for circadian rhythmicity, it follows that cells connecting upstream of the SCN will be involved in circadian entrainment. Experiments have been done using a modified retrograde rabies virus. Rabies viruses have the unique property that they jump synapses backwards, following inputs backwards toward the origin. When this virus was injected into the SCN, it followed most inputs back to the retina, implicating light as the feature of the natural world that governs our sleep/wake cycles. The neural pathway from the retina to the SCN is known as the retinohypothalalmic tract.

The specific retinal cells identified in the retina are a subtype of ganglion cell called the intrinsically photosensitive retinal ganglion cells (ipRGC). IpRGCs are relatively large cells that distribute their dendrites coarsely, creating a sparse, but complete, mosaic across the retina. The unique feature of these cells is that they are "intrinsically photosensitive." This is because they express a light sensitive protein called melanopsin, which is in the same class of protein as those found in rod and cone photoreceptors. The presence of melanopsin means that the ipRGC can respond to light directly without inputs from other neurons.

The discovery of a ganglion cell expressing a light sensitive molecule intrinsically, was surprising. This is because axons of the ganglion cells form the optic nerve of the eye serving the function of transmitting signal from the eye to the brain. Conventionally, ganglion cells were known to transmit signals from the photoreceptor cells of the eye (rods and cones) which function to transduce light energy into neural signals but not be light sensitive themselves.

To date, products involved in producing signals down the retinohypothalalmic pathway have focused on stimulating melanopsin inside the ipRGC. Melanopsin peaks at 480 nm, which is perceptually blue light. It also is sparsely distributed throughout the dendrites, requiring large amounts of light to directly activate the cell. However, despite the presence of melanopsin, ipRGCs do have inputs from other cell types. There are light sensitive cells upstream of the ganglion cells called rod and cone photoreceptors. Cone and rod photoreceptors tile the back of the eye creating a high-density mosaic sufficient to mediate human vision, and both cones and rods exist in a geometric orientation where the long, cylindrical portion that is filled with light sensitive protein, is parallel to light entering the eye, increasing the probability of an interaction between light and the molecule. Being highly specialized for absorbing light rod and cone photoreceptor activation of ipRGCs occurs at light levels about 1,000 lower than lights that stimulate ipRGCs directly.

Rod photoreceptors serve vision under dim light as occurs at night while cones are responsible for daytime vision.

Cones are of three types long-wavelength-sensitive (L), middle wavelength-sensitive (M), and short wavelength-sensitive (S). The words long, middle, and short refer to the part of the electromagnetic spectrum to which the molecule is tuned, giving rise to the commonly recognized terms used to describe them; red, green, and blue cones, respectively.

Cones and rods are both upstream of the ipRGC. When they are activated, the retinal wiring upstream leads to either excitation or inhibition onto the ipRGC. The S-cone input to ipRGCs is inhibitory. Thus, ipRGCs are inhibited by the onset of S-cone stimulating lights and they are excited by their offset. When M- and L-cones are activated, they excite the ipRGC sending action potentials to the SCN (FIG. 5). Rods also feed into the ipRGC in an excitatory way.

The spectral tuning of melanopsin is 480 nm, L-opsin peaks between 555 and 559 nm in color-normal humans, M-opsin peaks at 530 nm, and S opsin peaks at 419 nm. FIG. 6 illustrates the relative photopigment curves in humans, showing where each receptor is responsive to photons within each waveband.

Melanopsin inside the ipRGC and the L+M cones activate the ipRGCs with the relative amount of light required being designated by the photopigment curves. Light stimuli that activate S-cones inhibit the ipRGC activity, and the offset of S-cone activation releases inhibition on the ipRGC causes action potentials in the ipRGC.

FIG. 4 illustrates the activity of ipRGCs from the L and M cones when first triggered by the peak respective wavelengths. As shown, ipRGCs produce transient responses to cone stimuli, being most active immediately after light onset, but with the activity slowing even though the light stimulation continues. Alternatively, the ipRGCs are inhibited when the S cones stimulated; but when the S cones are not activated the ipRGCs can be activated but lights that stimulate L and M cones and melanopsin as shown in FIG. 3.

Previously in designing lights capable of manipulating human circadian rhythms, mood, alertness and sleep it has been assumed that melanopsin, the nonvisual opsin present in ipRGCs is the main photopigment involved in circadian photoentrainment in vertebrates, suggesting that contributions from other pigments can be ignored. This is true under laboratory conditions in which these ideas have been tested. Melanopsin is best stimulated by steady, diffuse, bright light. However, because ipRGC responses to rod and cone contributions are transient and rod inputs saturate at high light levels, bright diffuse steady lights are poor stimuli for rod and cone inputs to the circadian system. However, the situation is reversed in the natural world where there are frequent transitions between light and shadow and where the light bombarding the eye constantly changes color as an animal darts through its environment. The response thresholds of the ipRGCs are orders of magnitude lower for brief increments of colored light incident on the cones than for the same lights acting on the intrinsic photopigment; thus, under many natural conditions, the melanopsin contribution becomes negligible. Thus, modulating the temporal and chromatic properties of the light output as disclosed herein provides a much more natural and effective stimulus for manipulating circadian phase and influencing activity rhythms, mood, arousal and sleep.

Besides its role in circadian behavior, the non-image forming visual system that receives input from ipRGCs also is responsible for the pupillary light response. Bright lights cause to pupil to constrict saving the eye from light damage. It is beneficial that the pupil remain constricted as long as damaging light levels are present. The pupillary light response cannot be driven by rods and cones because ipRGCs only respond transiently to their stimulation. Thus, in natural world the intrinsic photopigment in ipRGCs serves as a protective mechanism keeping the pupils constricted under very high light levels. However, under natural conditions stimulation of the rods and cones is the most important mediator of circadian photoentrainment.

Cone photoreceptors originally evolved to provide animals with information about circadian time in the natural world, and that this system continues to serve this function in humans. The sustained response characteristics produced by melanopsin are ideally suited to drive the pupillary light reflex, suggesting that it evolved for that purpose. The fact that melanopsin can provide significant input to the circadian system under conditions where rods and cones are disabled, such as in animals with photoreceptor degeneration or in the case of exposure to bright, steady, uniform laboratory lighting is apparently a vestige of the suprachiasmatic nucleus (SCN) and olivary pretectal nucleus (OPN) both using information from the retina that is multiplexed on the same ganglion cell conduit.

While it is true that previous methods designed to stimulate ipRGCs by driving melanopsin are effective when they produce painfully high light levels of >5,000 lux, a much more natural and efficient method to accomplish the same end is described here.

Disclosed methods involve a light source that targets color opponent inputs to ipRGCs from the L-, M- and S-cone photoreceptors and modulates them chromato-temporally to drive the circadian rhythm entrainment pathway. Knowing that the ganglion cell responsible for synapsing into the circadian rhythm centers in the brain has converging L- and M-cone excitatory inputs and inhibitory S-cone input, the light source produces L+M and S stimulation 180 degrees out of phase from one another. L- and M-cones feed this system in the same sign, therefore combined they have a maximum sensitivity of about 550 nm, but with sufficient sensitivity to drive them between about 500 and 630 nm. S-cones are maximally sensitive to 419 nm, but lights between 400 and 480 nm can produce strong S-cone responses. Examples involve producing a light that will be useful to produce activity in the ipRGCs (circadian pathway) to synchronize the SCN master clock and stimulate other centers involved in circadian rhythm, mood, activity, arousal and sleep. The chromato-temporal nature of the light exploits that fact that the high firing rate the ipRGCs result from the upstream L+M vs S cone signaling. The short wavelength stimulus suppresses activity in the ipRGC therefore priming it. When the L+M stimulus is exchanged for the S, immediate and fast firing trains of action potentials are sent down the axon to the SCN. Alternation of L/M and S stimuli results in strong continuous activation of the ipRGCs.

Temporally, various waveforms that can be used for generating the L+M and the S stimuli which will ultimately excite the ipRGC. Square, sine, and ramp waves will work, as well as other timings that modulate between the L+M and S chromatic stimuli may achieve desired results. Cones are unable to respond to very high temporal frequencies. Also, bursts of maximal firing rate in the ipRGCs are only sustained for short durations, making low frequency stimulation suboptimal. Therefore, target modulation frequencies to achieve maximum signaling down the ipRGC pathway is between 0.1 and 100 Hz. Duty cycles between L+M and S stimulation are implemented at 50%, although L+M 1%<duty cycles<99% will produce significant responses.

The light sensitive molecule intrinsic to the ipRGCs (melanopsin ganglion cell) has a peak sensitivity of 480 nm. Stimulation by light centering at 480 nm +/−20 nm can directly stimulate the pathway, but to activate the intrinsic photopigment molecule light intensities should be at least 5000 lux. Previous methods for driving the retinohypothalamic pathway have attempted to directly stimulate the intrinsic melanopsin molecule (e.g. blue light Seasonal Affective Disorder (SAD) lights). The reason why higher intensity light is required is because of the low molecular density of melanopsin inside the ganglion cell, ipRGCs make up less than 0.2% of all cells that are light sensitive, and because the orientation and shape of the ipRGC creates a low surface area where light can interact with the molecule. Previously, intensities of diffuse, steady blue lights less than 5000 lux and broadband "white" light less than 10,000 lux have been shown to be insufficient to stimulate the retinohypothalamic pathway. In contrast, the cone photoreceptors upstream of the ipRGC can operate at less than 1 lux. Thus, significantly lower light levels can be used for more comfortable user experience and small, portable products with long battery lives to be produced that are as effective as large desk lights that produce 10,000 lux.

FIG. 7 shows a phase response curve. Relative to an individual's endogenous circadian phase, light pulses from the light source described in this disclosure given at different times of day may either (1) do nothing, (2) phase delay, or (3) phase advance an individual. The dotted line in FIG. 8 graphically represents circadian rhythm phase advance. To advance the circadian rhythm, L+M vs S cone driven responses through the ipRGC should occur in the area above the horizontal axis in FIG. 7. FIG. 9 graphically represents circadian rhythm phase delay. To delay the circadian rhythm, L+M vs S cone signal through the ipRGC should occur below the horizontal axis of FIG. 7. (Czeisler) Reference: "A phase response curve to single bright light pulses in human subjects", Sat Bir S. Khalsa, Megan E. Jewett, Christian Cajochen and Charles A. Czeisler.

FIG. 10 represents a spectral power curve for a commercially viable constant or steady state light source that would be useful for traditional work shifts, where humans are on a similar circadian rhythm, to create a phase advance in circadian rhythm to peak earlier in the day, and a phase delay for synchronization in the afternoon. This type of advance-delay cycle simulates the natural accordion effect of sunlight to set, reset, and synchronize circadian rhythm in humans; but with higher efficacy as the focus is on the L+M cone photoreceptors by using a higher percentage of total luminous flux in the 500-630 nm wavelength range. This is not as productive for high phase shift rates as the alternated peak wavelength light sources, but will trigger steady ganglion cell response and influence the circadian phase.

For example, an 800-lumen light source, with the higher percentage of 500-630 nm light will excite more ipRGC activity due to the higher probability of photons targeting L+M cone photoreceptors; as opposed to an 800 lumen light source with a higher percentage of light in the peak blue (480 nm) wavelength range to target melanopsin ganglion cells. Because interior lighting doesn't have illuminance values as high as sunlight, directly replicating the full spectral curve of sunlight will be less efficacious as sunlight during day peaks between 440-500 nm.

Other recent research, however, has demonstrated that the contribution of melanopsin alone may not be responsible for synchronizing circadian activity outside of the artificial photoperiods used in the laboratory. Mice lacking rods fail to entrain to experimental photoperiods with illumination of less than 1 lux (Ebihara and Tsuji, 1980 and Mrosovsky, 2003). Furthermore, mice lacking a middle-wavelength-sensitive cone, but with intact melanopsin ganglion cells, could not entrain to standard laboratory photoperiods of 10 lux or to a 15 min pulse of 530 nm light, but could entrain to 15 min pulses of 360 nm and 480 nm light (Dkhissi-Benyahya et al. 2007). Thus, a circadian system reliant upon melanopsin alone would be insensitive to the longer wavelengths of light prevalent at dawn and dusk, and this effect was recapitulated within our experiments.

The previous example refers to the probability of hitting L+M cone photoreceptors with photons being orders of magnitude higher than the probability of photons hitting melanopsin ganglion cells; thus with the total number of photons available being equal in each range, comparing two different sources, a light source peaking in the L+M opsin range will trigger more ganglion cell activity.

Example Embodiments

A modulating light source using LED(s), but not limited to, consisting of violet light peaking at a wavelength between 400-480 nm and a minimum peak illuminance of 0.1 lux at the eye, and a light peaking at a wavelength between 500-630 nm and a minimum peak illuminance of 0.1 lux at the eye; opposing modulation consisting of, but not limited to square, sine, or triangular waves of less than 100 Hz for the purpose of causing an advance or delay in circadian rhythm; use as a therapy light for seasonal affect disorder; and/or use as a mood enhancer.

A modulating light source using LED(s), but not limited to, consisting of violet light peaking at a wavelength between 400-480 nm and a minimum peak illuminance of 0.1 lux at the eye with the presence of ambient light, whereas the modulation consists of, but not limited to square, sine, or triangular waves of less than 100 Hz for the purpose of causing an advance or delay in circadian rhythm; use as a therapy light for seasonal affect disorder; and/or use as a mood enhancer.

A steady light source using LED(s), but not limited to, fixed at 0 Hz or modulating at frequencies greater than 0.1 Hz, consisting of light sources with peak wavelength between 470-580 nm, with the addition of lower percentage luminance of high CRI white light sources for the purpose to focus on L and M-opsin production for photoentrainment in commercial settings as use for a circadian synchronizer, therapy for seasonal affect disorder, and use as mood enhancement for increased productivity.

A steady light source using LED(s), but not limited to, fixed at 0 Hz or modulating greater than 0.1 Hz, consisting of peak wavelength between 600-700 nm with the addition of lower spectral power white light source with a high CRI to chromatically shift the white light source for the purpose of illumination as a circadian non-disruptor.

A high CRI LED that uses phosphors to create a chromatically shifted LED with a peak wavelength between 470-580 nm, or a mix of LEDs within a lamp to achieve the same high CRI light with peak wavelength between 470-580 nm, for the purpose to focus on L and M-opsin production for photoentrainment in commercial settings as use for a circadian synchronizer, therapy for seasonal affect disorder, and use as mood enhancement for increased productivity.

A luminaire with architectural, task, area, and reading lighting applications that use light sources in any of the previous examples.

Personal wearable device applications such as goggles, headbands, arm and wristwear that use light sources in any of the previous examples.

Automotive and aerospace dash, accent, and cabin general illumination applications, and automotive headlights that use light sources in any of the previous examples.

Portable illuminating devices that use light sources in any of the previous examples.

Medical therapy or ambient devices that use light sources in any of the previous examples.

Backlighting for displays such as cell phones, tablets, computer monitors, televisions, and related that use light sources in any of the previous examples.

A luminaire or lamp used for infants and children that use light sources in any of the previous examples.

A wearable device that is used for shining light onto the retina while subjects are asleep that use light sources in any of the previous examples.

An example is a low intensity flickering light source, with a minimum illuminance of 0.1 lux at the eye, that uses the combination of a short and long wavelength light sources to shift or synchronize circadian rhythm of humans by triggering intrinsically photosensitive retinal ganglion cells. The example is also a higher CRI commercial ready steady-state light source that focuses more on L+M cones RGCs stimulation to shift or synchronize circadian rhythms naturally. The example includes the applications that use the flickering light source in architectural, portable, personal, automotive, and medical devices to shift circadian rhythm in humans.

An example includes a high CRI "white" LED with peak wavelength between 480-580 nm with the presence of light in the visible spectrum from 400-780 nm.

An example includes a lamp that uses a combination of the plurality discrete LEDs with a peak between 480-560 nm mixed with high CRI "white" LED's to create a light output that has a peak wavelength between 480-580 nm with the presence of light in the visible spectrum from 400-780 nm.

An example includes modulating light within the L+M opsin photosensitivity range along with violet light in the S photosensitivity range to generate a high level of ganglion cell activity by firing, then immediately inhibiting activity in ganglion cells. This is due to L+M ganglion cells being most active immediately after being triggered, then shut off so they can be fired again; along with S ganglion cells being active immediately after elimination of violet light. Compared to blue light, this is a higher efficacy use of photons to influence circadian phase.

This can be done with modulating blue (melanopsin) and violet light as well; but since half the photons of blue light actually make it through the lens, and melanopsin ganglion cells are far fewer and smaller than L+M cones, the probability of photons targeting melanopsin ganglion cells is much lower than photons targeting L+M ganglion cells.

Targeting L+M ganglion cells is more efficacious than targeting Melanopsin ganglion cells with both modulating and steady light.

Melatonin is not a circadian phase driver; Melatonin is a hormone and is only an indicator of circadian phase, it is lowest when a person is at peak phase (~noon), and highest when person is at base phase (~midnight).

Measuring melatonin levels in humans is used as circadian phase indication due to the ease of melatonin measurement in saliva and blood. Other hormones can be used as circadian phase indicators as they peak and valley during specific points of circadian phase, but aren't as easily measured for correlation. Many people confuse melanopsin and melatonin as being related, but there is no correlation.

Visible wavelengths of light do not suppress or generate melatonin secretion. The body produces the hormone melatonin at varying levels throughout the day as a result of phase synchronization in the human body regardless of presence of visible light.

All hormones in the human body will synchronize accordingly to circadian phase. Proteins (opsins), not hormones (such as melatonin), are what is generated and inhibited in the retina by visible light.

Circadian phase advances and delays can't be driven by visible light at anytime during the day. Circadian phase advance (peaking earlier) only occurs before the individual peaks; and circadian phase delays (dipping later) only occurs after the individual peaks.

As used herein, the term "correlated color temperature (CCT)" may refer to the apparent color of light emitted from the characterized light source as compared to the color of light emitted by iron at each respective temperature in degrees Kelvin.

While various example aspects and example embodiments have been disclosed herein, other aspects and embodiments will be apparent to those skilled in the art. The various example aspects and example embodiments disclosed herein are for purposes of illustration and are not intended to be limiting, with the true scope and spirit being indicated by the following claims.

We claim:

1. A device comprising:
   a light source assembly; and
   a control system configured to cause the light source assembly to perform functions comprising:
      emitting a first light having one or more first wavelengths that are greater than or equal to 400 nanometers (nm) and less than or equal to 440 nm, wherein a first intensity of the first light oscillates at a first frequency; and
      emitting a second light having one or more second wavelengths that are greater than 440 nm, wherein a second intensity of the second light (i) oscillates at a second frequency that is equal to the first frequency and (ii) is out of phase with the first intensity.

2. The device of claim 1, wherein the first light includes no wavelengths greater than 440 nm.

3. The device of claim 1, wherein the first light includes no wavelengths less than 400 nm.

4. The device of claim 1, wherein the second light includes no wavelengths less than 440 nm.

5. The device of claim 1, wherein the first light and the second light take a form of waveforms having equal respective duty cycles.

6. The device of claim 1, wherein the first light and the second light take a form of waveforms having unequal respective duty cycles.

7. The device of claim 1, wherein the first frequency and the second frequency are greater than or equal to 0.03 Hz and less than or equal to 50 Hz.

8. The device of claim 1, wherein the device is a therapeutic wearable device configured for adjusting a circadian rhythm of a subject via the first light and the second light.

9. The device of claim 1, wherein a sum of the first intensity and the second intensity is substantially constant with respect to time.

10. The device of claim 1, wherein a first average of the first intensity over time is less than a second average of the second intensity over time.

11. A method comprising:
   emitting, by a lighting device, a first light having one or more first wavelengths that are greater than or equal to 400 nanometers (nm) and less than or equal to 440 nm, wherein a first intensity of the first light oscillates at a first frequency; and
   emitting, by the lighting device, a second light having one or more second wavelengths that are greater than 440 nm, wherein a second intensity of the second light (i) oscillates at a second frequency that is equal to the first frequency and (ii) is out of phase with the first intensity.

12. The method of claim 11, wherein the first light includes no wavelengths greater than 440 nm.

13. The method of claim 11, wherein the first light includes no wavelengths less than 400 nm.

14. The method of claim 11, wherein the second light includes no wavelengths less than 440 nm.

15. The method of claim 11, wherein the first light and the second light take a form of waveforms having equal respective duty cycles.

16. The method of claim 11, wherein the first light and the second light take a form of waveforms having unequal respective duty cycles.

17. The method of claim 11, wherein the first frequency and the second frequency are greater than or equal to 0.03 Hz and less than or equal to 50 Hz.

18. The method of claim 11, wherein emitting the first light and the second light causes adjustment of a circadian rhythm of a subject.

19. The method of claim 11, wherein a sum of the first intensity and the second intensity is substantially constant with respect to time.

20. The method of claim 11, wherein a first average of the first intensity over time is less than a second average of the second intensity over time.

* * * * *